US011589873B2

(12) United States Patent
Adawi et al.

(10) Patent No.: US 11,589,873 B2
(45) Date of Patent: Feb. 28, 2023

(54) OCCLUSION DETECTION BY PRESSURE MEASUREMENT

(71) Applicant: Biosense Webster (Israel) Ltd, Yokneam (IL)

(72) Inventors: Eid Adawi, Tur'an (IL); Eliyahu Ravuna, Kiryat Ata (IL); Shmuel Auerbach, Kerem Maharal (IL); Nakdimon Nissim Levy, Pardes Hana (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/720,978

(22) Filed: Dec. 19, 2019

(65) Prior Publication Data
US 2020/0205840 A1    Jul. 2, 2020

Related U.S. Application Data

(60) Provisional application No. 62/786,982, filed on Dec. 31, 2018.

(51) Int. Cl.
*A61B 17/12*    (2006.01)
*A61B 17/00*    (2006.01)

(52) U.S. Cl.
CPC ............... *A61B 17/12122* (2013.01); *A61B 2017/00022* (2013.01); *A61B 2017/00243* (2013.01); *A61B 2562/0247* (2013.01)

(58) Field of Classification Search
CPC .... A61B 17/12122; A61B 2017/00243; A61B 17/12168–12177; A61B 2017/1205;
(Continued)

(56) References Cited

U.S. PATENT DOCUMENTS

2008/0097422 A1    4/2008  Edwards et al.
2011/0144637 A1    6/2011  Pageard et al.
(Continued)

FOREIGN PATENT DOCUMENTS

WO    2013/009872 A1    1/2013
WO    2017/066197 A1    4/2017

OTHER PUBLICATIONS

International Search Report and Written Opinion dated Apr. 1, 2020 for PCT International Application No. PCT/IB2019/061338.

*Primary Examiner* — Darwin P Erezo
*Assistant Examiner* — Raihan R Khandker
(74) *Attorney, Agent, or Firm* — Volpe Koenig

(57) ABSTRACT

A system, device and method for left atrial appendage occlusion detection is disclosed. The system for occlusion detection comprises a sheath; a delivery system comprising: a delivery catheter extending between a proximal end and a distal end; and a handle coupled to the proximal end of the delivery catheter; a medical tool coupled to a distal end of the delivery catheter at a target location within a portion of an organ of a patient, the medical device comprising a hub including a bore defining an axis, an occluder portion coupled to the hub and an anchor portion extending between a first end and a second end; at least one pressure sensor configured to measure a pressure of the target cavity while blood is suctioned form inside the left atrial appendage; and at least one processor configured to process the pressure measurement acquired from the at least one pressure sensor.

9 Claims, 19 Drawing Sheets

(58) Field of Classification Search
CPC .......... A61B 2017/12054; A61B 2017/00022; A61B 2562/0247; A61B 5/021; A61B 17/0057; A61B 2017/00575; A61B 17/12172; A61M 2025/0001; A61M 2025/0002; A61M 2025/0003
See application file for complete search history.

(56) References Cited

U.S. PATENT DOCUMENTS

| | | |
|---|---|---|
| 2014/0276709 A1 | 9/2014 | Wittenberger et al. |
| 2014/0276789 A1 | 9/2014 | Dandler et al. |
| 2014/0364941 A1 | 12/2014 | Edmiston et al. |
| 2015/0157326 A1* | 6/2015 | Schiemanck ........ A61B 5/6869 606/194 |
| 2015/0374448 A1* | 12/2015 | Katz ................... A61B 90/06 600/424 |
| 2016/0045165 A1 | 2/2016 | Braido et al. |
| 2016/0045316 A1* | 2/2016 | Braido ................. A61B 5/026 623/2.38 |
| 2016/0157914 A1 | 6/2016 | Avitall |
| 2020/0000367 A1* | 1/2020 | Oren .................... A61B 5/062 |
| 2020/0093991 A1* | 3/2020 | Schwartz ............ A61M 5/172 |

\* cited by examiner

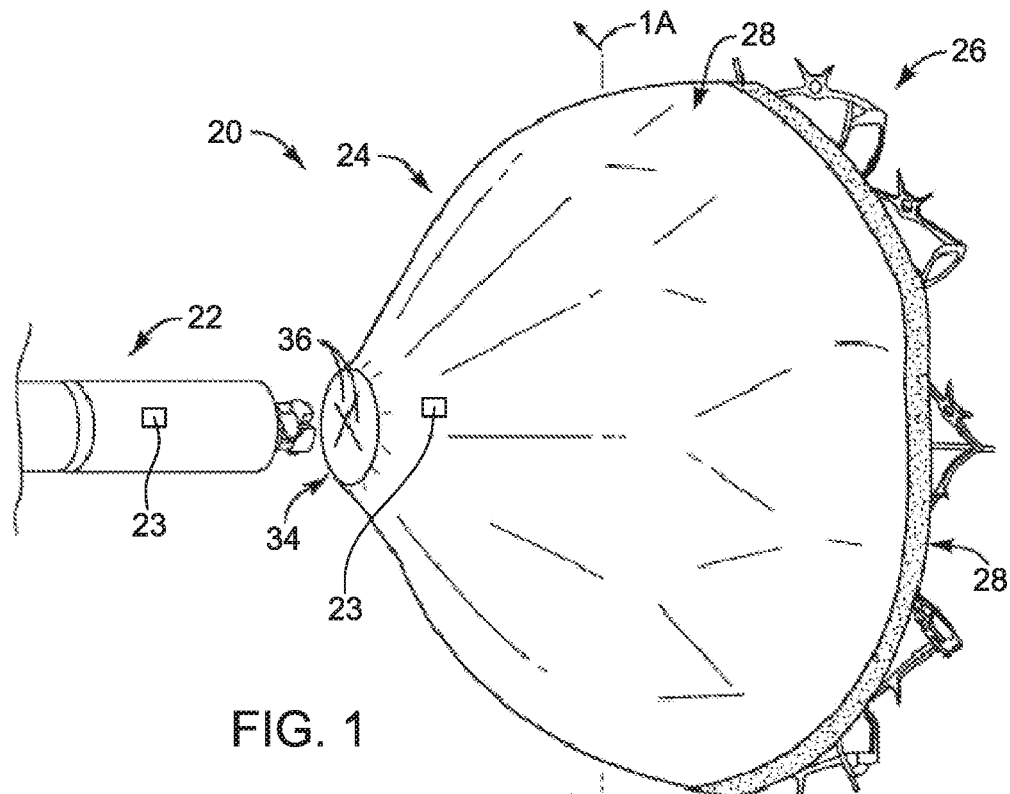
FIG. 1
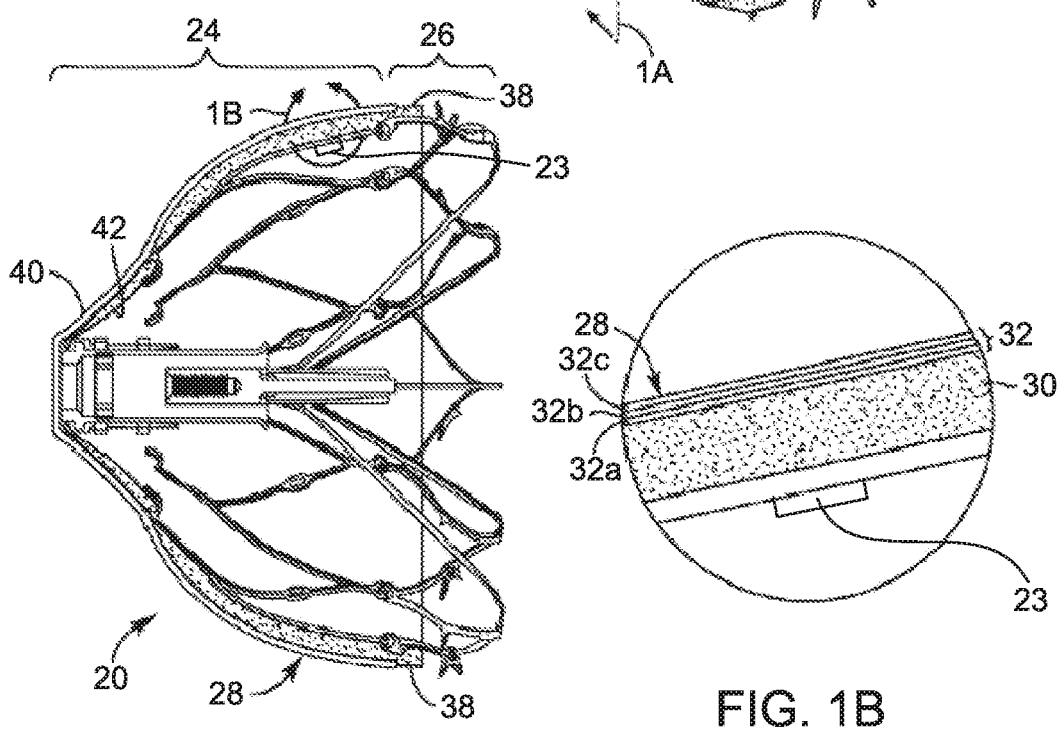
FIG. 1A
FIG. 1B

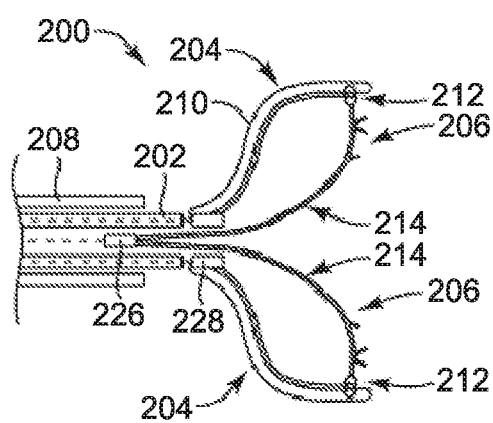
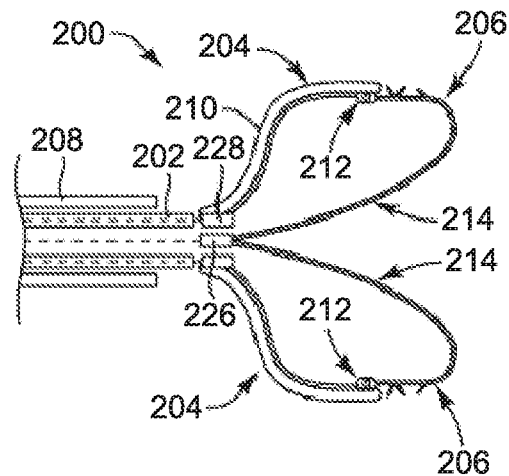
FIG. 14A    FIG. 14B
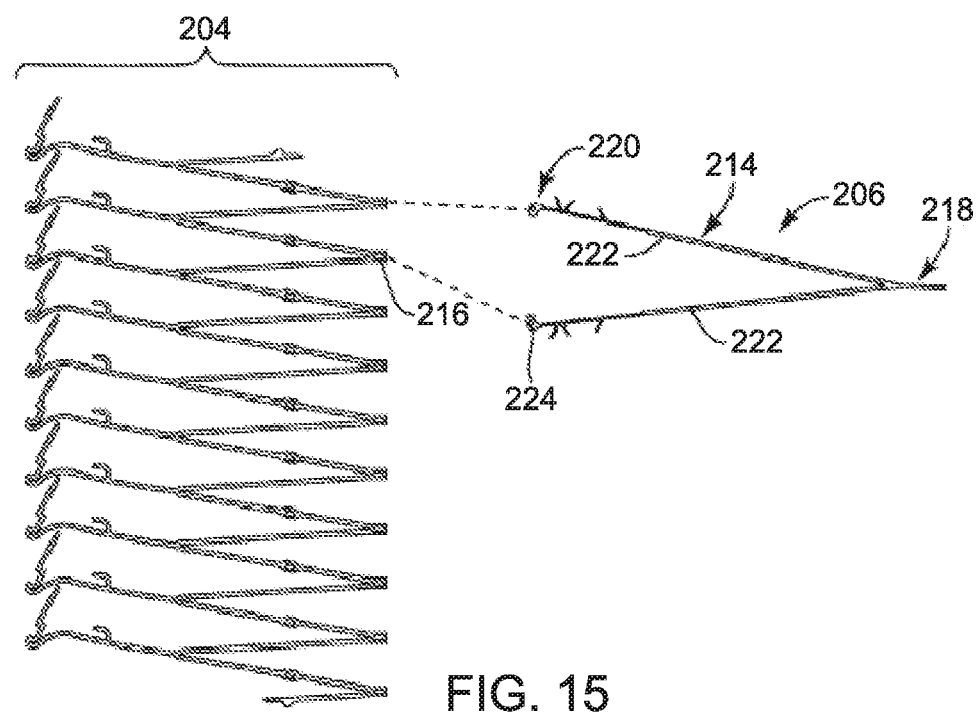
FIG. 15

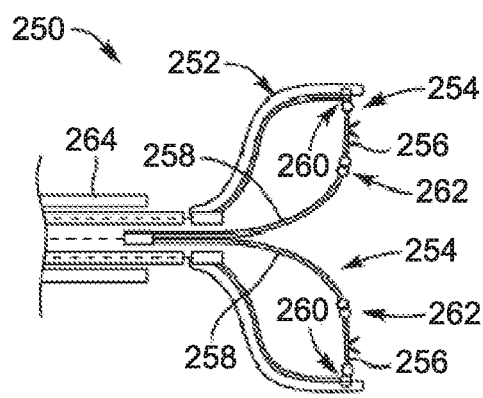
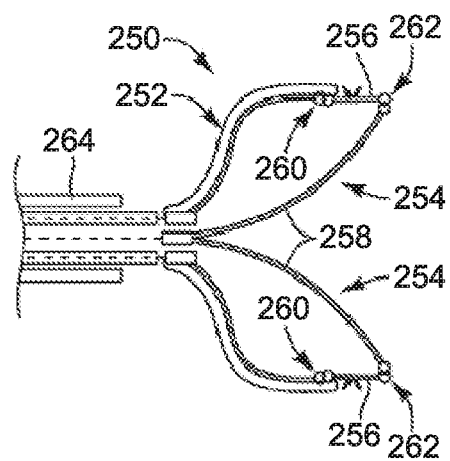
FIG. 16A        FIG. 16B
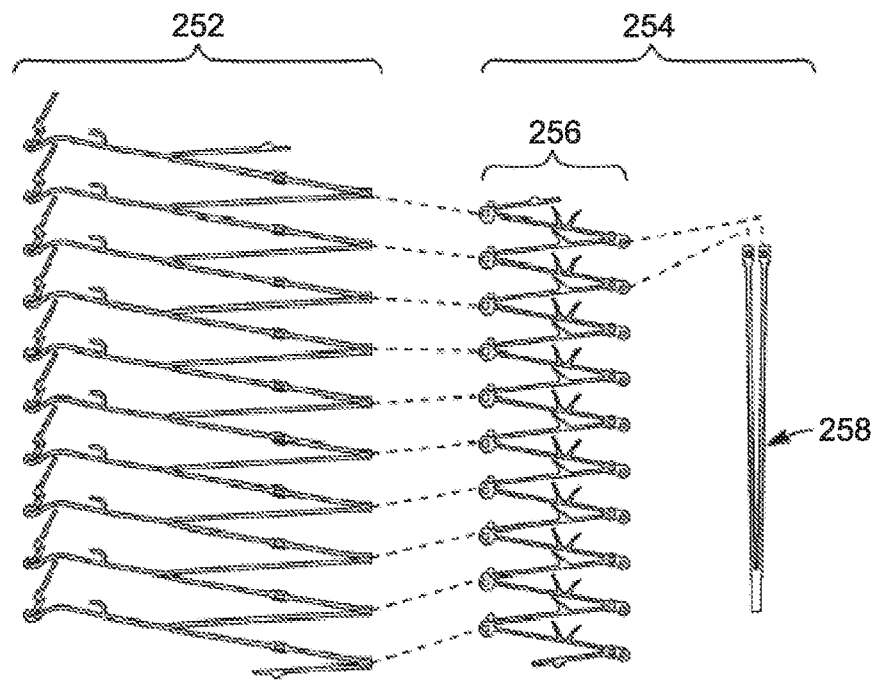
FIG. 17

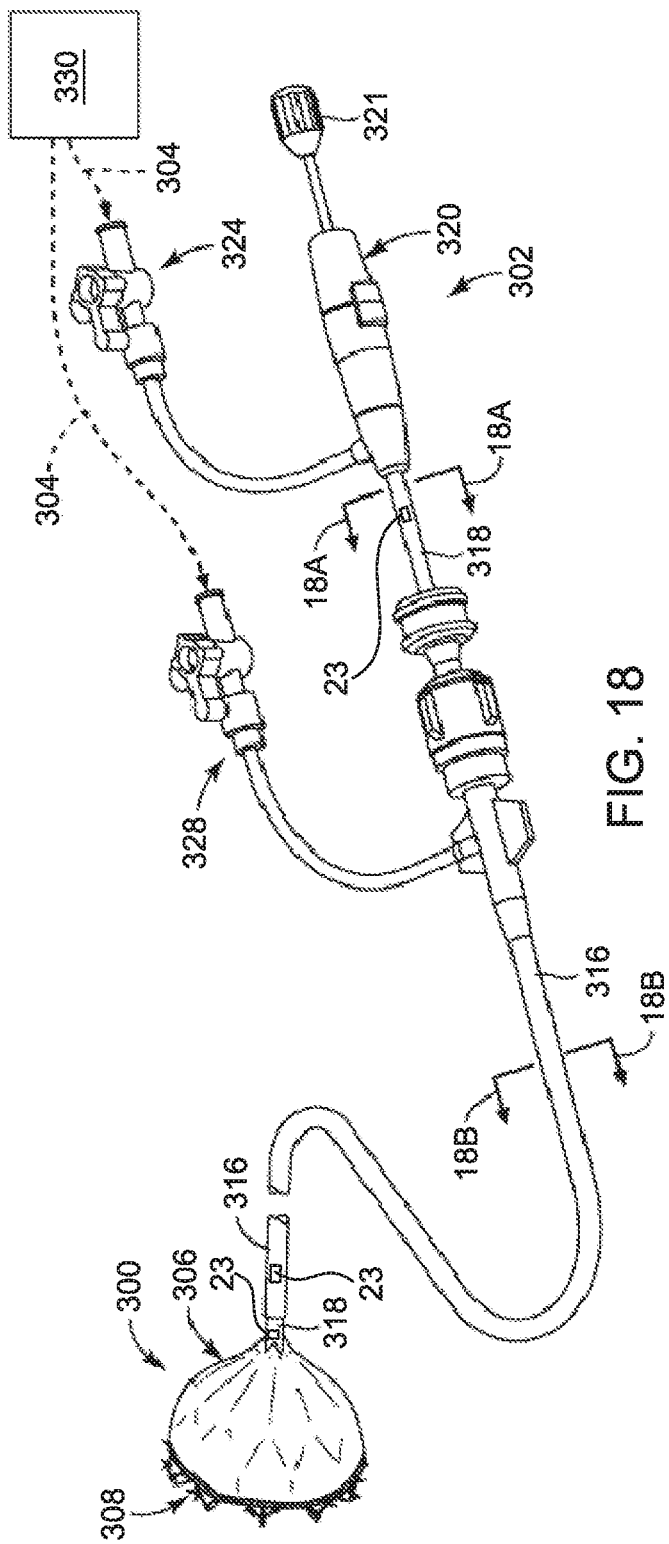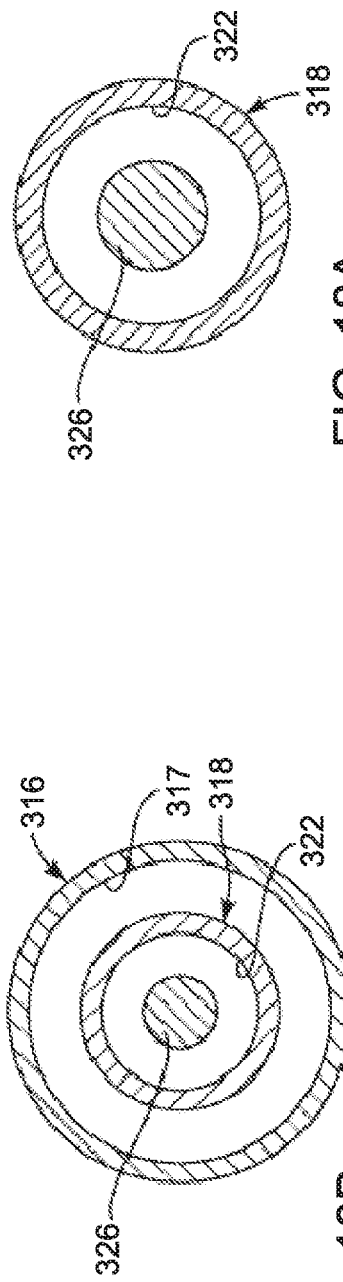

OCCLUSION DETECTION BY PRESSURE MEASUREMENT

CROSS-REFERENCE TO RELATED APPLICATIONS

This application claims the benefit of U.S. Provisional Application No. 62/786,982 filed on Dec. 31, 2018, the content of which is hereby incorporated by reference herein.

This application incorporates herein by reference as if fully set forth the contents of a non-provisional application titled Occlusion Detection Via Fluid Dilution being filed on the same day as this application. That non-provisional application claims the benefit of U.S. Provisional Application Nos. 62/786,957, filed on Dec. 31, 2018 and 62/786,997, also filed on Dec. 31, 2018. This application incorporates herein by reference as if fully set forth the contents of both of those provisional applications.

BACKGROUND

The upper chambers of the heart, the atria, have appendages attached to each of them. For example, the left atrial appendage is a feature of all human hearts. The physiologic function of such appendages is not completely understood, but they do act as a filling reservoir during the normal pumping of the heart. The appendages typically protrude from the atria and cover an external portion of the atria. Atrial appendages differ substantially from one to another. For example, one atrial appendage may be configured as a tapered protrusion while another atrial appendage may be configured as a re-entrant, sock-like hole. The inner surface of an appendage is conventionally trabeculated with cords of muscular cardiac tissue traversing its surface with one or multiple lobes.

The atrial appendages appear to be inert while blood is being pumped through them during normal heart function. In other words, the appendages don't appear to have a noticeable effect on blood pumped through them during normal heart function. However, in cases of atrial fibrillation, when the atria go into arrhythmia, blood may pool and thrombose inside of the appendages. Among other things, this can pose a stroke risk when it occurs in the left appendage since the thrombus may be pumped out of the heart and into the cranial circulation once normal sinus rhythm is restored following arrhythmia events.

Historically, appendages have sometimes been modified surgically to reduce the risk imposed by atrial fibrillation. In recent years devices which may be delivered percutaneously into the left atrial appendage have been introduced. The basic function of these devices is to exclude the volume within the appendage with an implant which then allows blood within the appendage to safely thrombose and then to be gradually incorporated into cardiac tissue. This process, coupled with the growth of endothelium over the face of the device, can leave a smooth, endothelialized surface where the appendage is located. In comparison to surgical procedures, devices implanted percutaneously are a less invasive means for addressing the problems associated with the left atrial appendage.

In general, occlusion is detected by injecting contrast fluid into a target cavity and observing whether the contrast fluid escapes from the target cavity. However, contrast fluid has several disadvantages, such as allergic reactions. It would be advantageous to provide a percutaneous system, method and/or device that is capable of left atrial appendage occlusion detection without the use of contrast fluid.

SUMMARY

A system, device and method for left atrial appendage occlusion detection is disclosed. However, it should be understood that the system, device and method of the present invention is not limited to use for detecting occlusion in the left atrial appendage and could be used for determining occlusions in other cardiac cavities. In addition, the present invention could be used for determining occlusions in other parts of the body, such as blockages in the coronary arteries or blood clots in the brain. The system for occlusion detection may include a sheath having a length and a sheath lumen extending through the length of the sheath; a delivery system comprising: a delivery catheter extending between a proximal end and a distal end; and a handle coupled to the proximal end of the delivery catheter; a medical tool coupled to a distal end of the delivery catheter at a target location within a portion of an organ of a patient, the medical device comprising a hub including a bore defining an axis, an occluder portion coupled to the hub and an anchor portion extending between a first end and a second end; at least one pressure sensor configured to measure a pressure of the target cavity while blood is suctioned from inside the target cavity; and at least one processor configured to process the pressure measurement acquired from the at least one pressure sensor.

A method of occlusion detection according to the present disclosure may include positioning a medical device coupled to a distal end of a delivery catheter at a target location within a portion of an organ of a patient, the medical device comprising an occluder portion, an anchor portion, a tissue growth member and a hub; deploying the occluder portion of the medical device and, upon the occluder portion being in an expanded, deployed position, actuating the anchor portion from a retracted position to an anchor deployed position; detecting, via at least one pressure sensor, a pressure of blood in the target cavity while blood is suctioned from inside the target cavity; and processing, via a processor, the pressure detected by the at least one sensor. The presence or absence of an occlusion is determined through at least one measurement of the pressure of the blood.

BRIEF DESCRIPTION OF THE DRAWINGS

FIG. 1 is a perspective view of a medical tool and a distal portion of a delivery system, accordingly to one embodiment of the present disclosure;

FIG. 1A is a partial cross-sectional view of the medical tool, taken along section line 1A of FIG. 1, according to another embodiment of the present invention;

FIG. 1B is an enlarged section view of an occluder portion, taken from detail 1B of FIG. 1A, according to another embodiment of the present invention;

FIGS. 14A and 14B are simplistic side profile views of another embodiment of a medical tool, depicting the medical tool in an anchor non-deployed position and an anchor deployed position, respectively, according to the present invention;

FIG. 15 is a top view of the occluder portion and the anchor portion of the medical tool of FIGS. 14A and 14B, depicting frame components cut from a flat sheet, according to another embodiment of the present invention;

FIGS. 16A and 16B are simplistic side profile views of another embodiment of a medical tool, depicting the medical tool in an anchor non-deployed position and an anchor deployed position, respectively, according to the present invention;

FIG. 17 is a top view of the occluder portion and the anchor portion of the medical tool of FIGS. 15A and 15B, depicting frame components cut from a flat sheet, according to another embodiment of the present invention;

FIG. 18 is a perspective view of a medical tool delivery system, depicting a medical tool attached and deployed at a distal end of the delivery system, according to another embodiment of the present invention;

FIG. 18A is a cross-sectional view of section 18A of FIG. 18, depicting a lumen defined in a proximal portion of a catheter of the delivery system, according to another embodiment of the present invention;

FIG. 18B is a cross-sectional view of section 18B of FIG. 18, depicting a sheath lumen of a sheath with the catheter of the delivery system therein, according to another embodiment of the present invention;

DETAILED DESCRIPTION OF THE PREFERRED EMBODIMENTS

Figure 2:
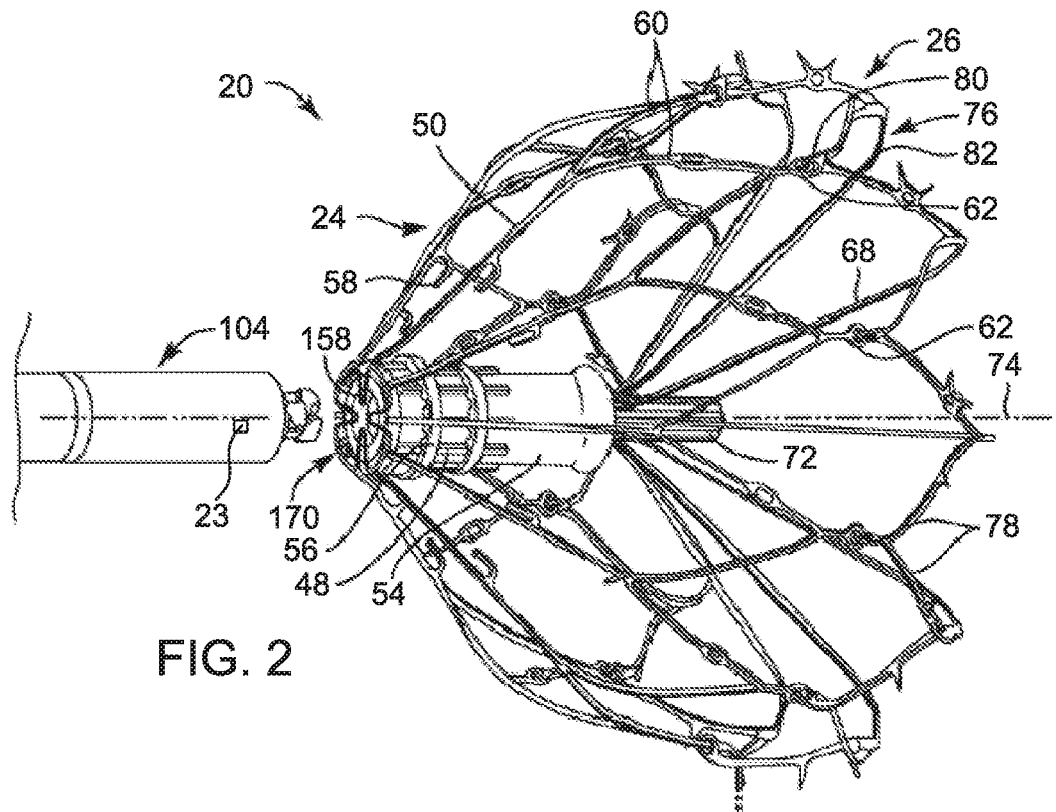
FIG. 2 is a perspective view of the medical tool of FIG. 1, depicting the frame without its tissue growth member, according to another embodiment of the present invention.

Embodiments of the present invention are directed to various devices, systems and methods of occlusion detection in a chamber in a body. For example, in one embodiment, a medical tool system for occlusion detecting in a left atrial appendage (LAA) of a heart is provided.

The system for occlusion detection comprises a sheath, a delivery system, a medical tool, at least one sensor and a processor. The sheath has a length and a sheath lumen extending through the length of the sheath. The delivery system comprises a delivery catheter extending between a proximal end and a distal end, and a handle coupled to the proximal end of the delivery catheter. The medical tool is coupled to a distal end of the delivery catheter at a target location within a portion of an organ of a patient. The medical tool comprises a hub including a bore defining an axis; an occluder portion coupled to the hub, the occluder portion configured to be moved to an occluder non-deployed position with the occluder portion within a distal portion of the sheath, and the occluder portion configured to be moved to an occluder deployed position upon the sheath being moved proximally relative to the occluder portion; and an anchor portion extending between a first end and a second end, the anchor portion having tines configured to engage tissue, the first end being coupled to the handle, the second end being pivotably coupled to a distal end portion of the occluder portion, wherein, upon the occluder portion maintaining the occluder deployed position, the anchor portion is pivotable relative to the occluder portion between an anchor non-deployed position and an anchor deployed position. The at least one sensor may be configured to detect at least one physical characteristic of blood. In an embodiment the at least one sensor is configured to measure pressure while blood is suctioned from the target cavity. Additionally or alternatively, the at least one sensor comprises at least one external pressure sensor that is connected to a proximal end of a lumen of the delivery catheter. The distal end of the lumen may be open to the blood pool of the target cavity, enabling the pressure of the target cavity to be measured directly. The at least one processor configured to process the blood characteristic data acquired from the at least one sensor.

In an embodiment, the at least one sensor is located on a distal portion of the sheath. Additionally or alternatively, the at least one sensor is located on the distal end of the delivery catheter. Additionally or alternatively, the at least one sensor is located on a proximal end of the delivery catheter.

In an embodiment, the tines of the anchor portion may be configured to engage with tissue within a LAA of the heart. In an embodiment, the processor may be further configured to compare the pressure acquired from the at least one sensor to a baseline pressure measurement. In an embodiment the processor may be configured to record measurements of pressure detected by the sensor over time. In a further embodiment, the system may further comprise a memory configured to store the measurements of pressure detected by the at least one sensor over time. In an even further embodiment, the system may further comprise a display configured to display the pressured detected by the at least one sensor. The display may further be configured to display a baseline characteristic of blood side by side or on top of the pressure detected by the at least one sensor over time. In an embodiment, the processor may be configured to determine whether an occlusion is present by how fast the pressure changes over a period of time.

A method of occlusion detection according to the present disclosure comprises positioning a medical device coupled to a distal end of a delivery catheter at a target location within a portion of an organ of a patient, the medical device comprising an occluder portion, an anchor portion, a tissue growth member and a hub; deploying the occluder portion of the medical device and, upon the occluder portion being in an expanded, deployed position, actuating the anchor portion from a retracted position to an anchor deployed position; detecting, via at least one pressure sensor, a pressure of blood in the target cavity; and processing, via a processor, the pressure detected by the at least one sensor. The presence or absence of an occlusion is determined through at least one measurement of the pressure of the blood. In an embodiment, the target cavity is a LAA.

In an embodiment, the detecting step is performed while blood is being suctioned from inside the target cavity. Additionally or alternatively, a pressure measurement may be performed directly using an external pressure sensor that is connected to a proximal end of a lumen of the delivery catheter. The distal end of the lumen may be open to the blood pool of the target cavity, enabling the pressure of the target cavity to be measured directly.

In an embodiment, the method further comprises determining a baseline pressure by positioning the medical device at a target location within a portion of an organ of a patient such that occlusion will not be established; deploying the occluder portion of the medical device and, upon the occluder portion being in an expanded, deployed position, actuating the anchor portion from a retracted position to an anchor deployed position having tines without establishing complete occlusion; injecting a fluid through the delivery catheter and through the hub of the medical device into a target cavity; detecting, via the at least one sensor, a pressure in the target cavity, and processing, via a processor, the pressure acquired from the at least one sensor and establishing the pressure as a baseline pressure measurement.

In an embodiment the method further comprising recording, via the processor, the pressure detected by the at least one sensor over time. In a further embodiment the method further comprises storing, in a memory, pressure measurements detected by the at least one sensor over time. The presence or absence of an occlusion may be determined by comparing the baseline pressure measurement to the detected pressure over time. In an embodiment, the method may further comprise determining, via a processor, the presence or absence of an occlusion by comparing the baseline measurement to the detected pressure over time.

Referring first to FIGS. 1 and 1A, a medical tool 20 and a distal end portion of a delivery system 22 is provided. The medical tool 20 and delivery system 22 may be employed in interventional procedures for percutaneously closing and modifying an opening or cavity such as, for example, a LAA within a heart (not shown). The medical tool 20 may include frame components of an occluder portion 24 and an anchor portion 26, the occluder portion 24 also including a tissue growth member 28 attached thereto. Further, the anchor portion 26 may be hingably coupled to the occluder portion 24 such that the anchor portion 26 may be actuated, upon deployment of the occluder portion 24, between a deployed position and a non-deployed position (not shown) via an actuation mechanism at a handle (not shown) of the delivery system 22. With this arrangement, the medical tool 20 and delivery system 22 may provide functionality of separating the steps of deploying the occluder portion 24 and the anchor portion 26, thereby, providing additional and enhanced functionality to the physician to properly position and implant the medical tool 20 in the LAA.

As set forth, the occluder portion 24 may include an occluder material or a tissue growth member 28 attached thereto. The tissue growth member 28 may be a porous material, or other cell attaching material or substrate, configured to promote endothelization and tissue growth thereover. The tissue growth member 28 may extend over a proximal side of the medical tool 20 and, particularly, over the occluder portion 24 and may extend over a portion of the anchor portion 26 and hinges coupling the anchor portion 26 to the occluder portion 24. As such, due to the shape of the frame components of the occluder portion 24, the tissue growth member 28 may include a proximal face that is generally convex to form an outer surface 40. The tissue growth member 28 may also include an inner surface 42 on its distal side that is generally concave shaped. In one embodiment, the tissue growth member 28 may extend primarily over an outside surface of frame components of the occluder portion 24 with a portion of the tissue growth member 28 extending on both the outside surface and the inside surface of the frame components of the occluder portion 24. In another embodiment, the tissue growth member 28 may extend primarily over both the outside surface and the inside surface of the frame components of the occluder portion 24 of the medical tool 20. In another embodiment, the tissue growth member 28 may extend solely over the outside surface of the frame components of the occluder portion 24.

With respect to FIGS. 1A and 1B, the tissue growth member 28 may include one or more types of materials and/or layers. In one embodiment, the tissue growth member 28 may include a first material layer 30 and a second material layer 32. The first material layer 30 may primarily be an underside layer or base layer of the tissue growth member 28. The first material layer 30 may include porous and conformable structural characteristics. For example, the first material layer 30 may include a foam type material, such as, a polyurethane foam or any other suitable polymeric material, such as a polymer fabric, woven or knitted. The second material layer 32 may include one or more layers of, for example, an expanded polytetrafluoroethylene (ePTFE) material. The second material layer 32 may be attached to an outer surface of the first material layer 30 with, for example, an adhesive. In one embodiment, the second material layer 32 may include a first layer 32A, a second layer 32B, and a third layer 32C such that the first layer 32A may be directly attached to the first material layer 30 and the third layer 32C may be an outer-most layer covering the proximal side of the medial device 20 with the second layer 32B extending therebetween. The various layers of the second material layer 32 may be bonded together by adhesives and/or by a thermal bonding heat process or other appropriate processes known in the art. In one particular example, the outer-most layers, such as the second and third layers 32B, 32C, may be formed of an ePTFE material having an internodal distance (sometimes referred to as pore size) of approximately 70 μm to approximately 90 μm. The first layer 32A of the second material layer 32, adjacent the first material layer 30, may be formed of an ePTFE material having a reduced internodal distance relative to the second and third layers 32B, 32C. For example, the internodal distance of the first layer 32A may be approximately 10 μm. This first layer 32A may be bonded or adhered to the first material layer 30 using an adhesive material. Any other suitable sized layers of ePTFE may be employed, such as ePTFE having an internodal distance up to about 250 μm. Further, there may be one or more additional layers, similarly sized to the first layer 32A, extending over a hub end 34 with flaps 36 (outlined with an "X" configuration) where the delivery system 22 interconnects with the medical tool 20 (see FIG. 1).

The second material layer 32 made of ePTFE effectively prevents the passage of blood, due to the small internodal distance and pore size of the first layer 32A, while the larger internodal distance of other layers (e.g., 32B and 32C) enable tissue in-growth and endothelization to occur. Additionally, the first material layer 30, being formed of a polyurethane foam, enables aggressive growth of tissue from the LAA wall into the tissue growth member 28 at the inside or concave side of the medical tool 20. Further, the first material layer 30 provides an exposed shelf 38 on the outer surface 40 around the periphery and distal end portion of the tissue growth member 28, which promotes aggressive fibroblast and tissue growth to further initiate endothelization over the outer surface 40 of the second material layer 32. It is noted that the use of appropriate adhesive materials between the first material layer 30 and the next adjacent layer 32A may also serve to fill in the pores of the next adjacent layer 32A and further inhibit possible flow of blood through the tissue growth member 28. Additional layers of ePTFE may also be included to the second material layer 32 of the tissue growth member 28.

Figure 3:
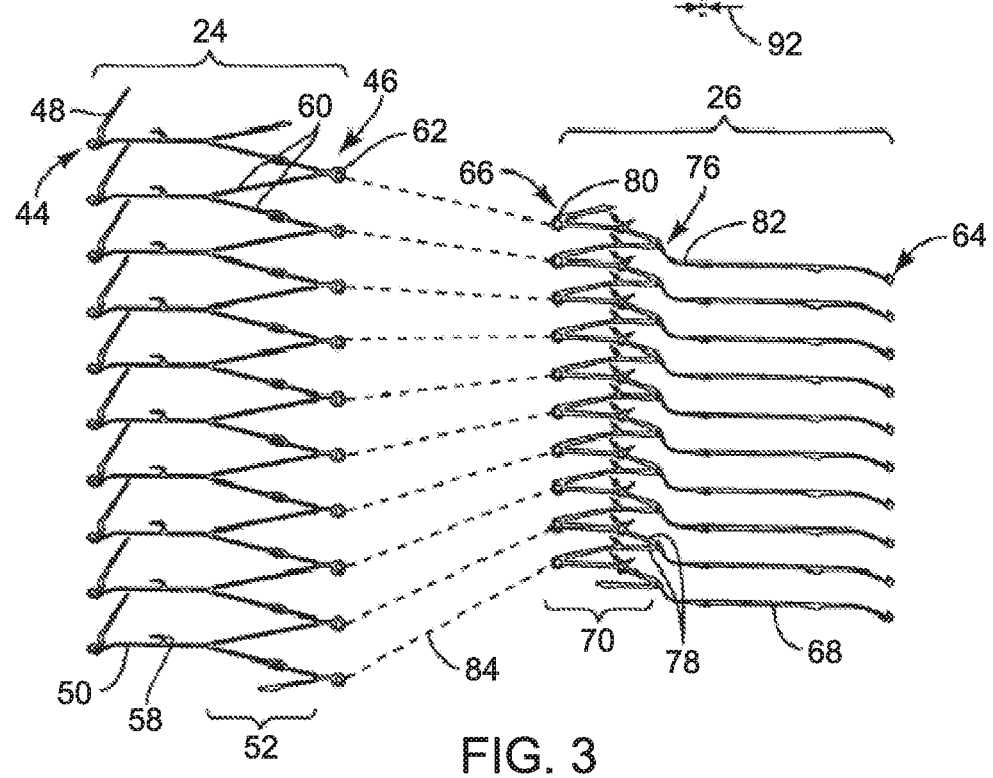
FIG. 3 is a top view of frame components of the occluder portion and the anchor portion of the medical tool of FIG. 2, depicting frame components laser cut from a flat sheet prior to being assembled, according to another embodiment of the present invention.

With reference to FIGS. 2 and 3, description of the medical tool 20 and its frame components will now be provided. FIG. 2 depicts the frame components in an assembled and fully deployed state and FIG. 3 depicts the frame components as cut from a flat sheet. As previously set forth, the medical tool 20 includes an occluder portion 24 and an anchor portion 26. The occluder portion 24 may include multiple occluder frame segments that may be interconnected to form the occluder portion 24. The occluder portion 24 may extend between a first end 44 and a second end 46 with face struts 50 and an occluder zig-zag portion 52 therebetween. Further, the occluder portion 24 includes base extensions 48 extending from the first end 44. The base extensions 48 may be coupled to a hub 54 via rings 56 with notches defined at an inner diameter in the rings 56. Each base extension 48 may extend from a proximal most portion of the occluder portion 24 or first end 44, the first end 44 being one end of each base extension 48 and face strut 50. Each base extension 48 may be sized and configured to be positioned around the hub 54 and held by one or more rings 56. Each base extension 48, at the first end 44, may extend to one face strut 50 of the occluder portion 24, the face strut 50 extending radially and distally from the first end 44. Each face strut 50 may include an extension 58 on a back side thereof, the extension 58 having a hook configuration sized and configured to hold a portion of the tissue growth member (not shown). Further, each face strut 50 extends to a v-extension 60 of the occluder zig-zag portion 52 such that distal ends of each v-extension 60 may be coupled to distal ends of adjacent v-extensions 60 (side-by-side) to define the occluder zig-zag portion 52. The occluder zig-zag portion 52 may enlarge radially and distally from the face struts 50 to a distal end or the second end 46 of the occluder portion 24. At the second end 46, the occluder portion 24 may include an occluder eyelet 62 sized configured to hingably couple to the anchor portion 26.

The anchor portion 26 may include multiple anchor frame segments that may be interconnected to form the anchor portion 26. The anchor portion 26 may extend between a first end 64 and a second end 66 with anchor actuator arms 68 and an anchor zig-zag portion 70 therebetween. The anchor actuator arms 68 may extend between the first end 64 and the anchor zig-zag portion 70. Each anchor actuator arm 68 may be configured to couple to a collar arrangement or splined sleeve 72 at the first end 64 of the anchor portion 26 such that the anchor actuator arms 68 are coupled as a unit or together via the splined sleeve 72. The splined sleeve 72 may be configured to actuate along an axis 74 of the medical tool 20 to move the anchor portion 26 between the anchor deployed position and anchor non-deployed position (not shown), discussed in more detail hereafter.

Figure 3A:
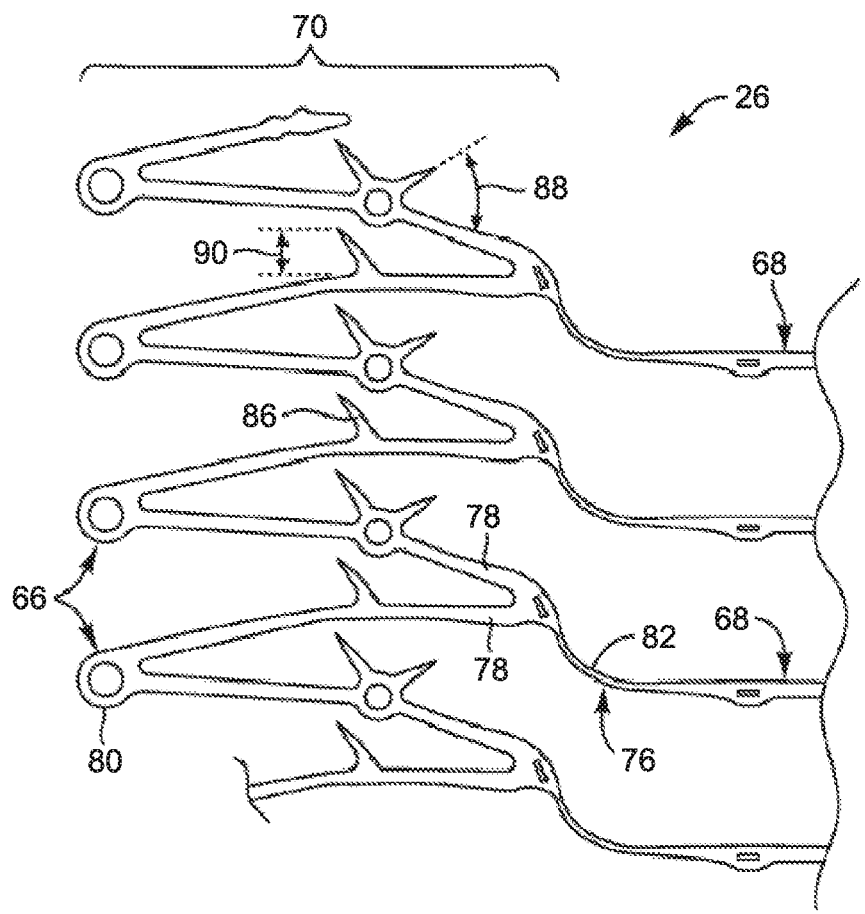
FIG. 3A is a partial enlarged view of the anchor portion depicted in FIG. 3, according to another embodiment of the present invention.

With reference now to FIGS. 2, 3, and 3A, the anchor actuator arms 68 may also include a flexure portion 76. The flexure portion 76 defines a taper 82 and radius extending along the radial length of the flexure portion 76 toward the anchor zig-zag portion 70 and then widens again at the anchor zig-zag portion 70. Such taper 82 along the radial length in the flexure portion 76 facilitates repetitious movement of the anchor portion 26 between the deployed position and the non-deployed position while also maintaining structural integrity of the anchor portion 26, and minimizing the stress and strain in the flexure portion 76 while facilitating a tight radius or loop. In one embodiment, the anchor actuator arms 68 may each include a coil (not shown) that may be wound around a portion of the actuator arm and over the flexure portion 76 with the ends of the coil secured to the anchor actuator arm 68. Such coil may substantially capture the anchor actuator arm 68 from extending in undesirable locations in the LAA should there be a fracture or break in the anchor actuator arm 68.

Each flexure portion 76 of the anchor actuator arms 68 may extend to anchor v-extensions 78 such that the proximal ends of each anchor v-extension 78 may be coupled to proximal ends of adjacent anchor v-extensions 78 (similar to the occluder zig-zag portion 52) to form the anchor zig-zag portion 70. At the interconnection of the proximal ends of the anchor v-extensions 78 or the second end 66 of the anchor portion 26, such proximal ends define an anchor eyelet 80. The anchor eyelet 80 may be sized and configured to hingably couple to a corresponding occluder eyelet 62 of the occluder portion 24, as shown by dotted lines 84 (see FIG. 3).

With respect to FIG. 3A, the anchor struts or anchor v-extensions 78 of the anchor zig-zag portion 70 may include one or more hooks 86 or barbs that may extend at an acute angle 88 from the anchor portion 26 or anchor v-extensions and remote from the occluder portion 24. Such acute angle 88 may range between about forty-five degrees and about sixty degrees. Further, the hooks 86 may extend from the anchor v-extensions 78 with a predetermined height 90 so as to provide effective engagement with a tissue wall within the LAA, but not to the extent of piercing all the way through the tissue wall to cause effusions in the LAA. The hooks also include a thickness 92 (see FIG. 2). Such thickness 92 may be similar to the thickness of sheet material from which the frame components (i.e., occluder portion 24 and anchor portion 26) of the medical tool 20 are cut.

With respect to FIG. 3, the occluder portion 24 and the anchor portion 26 are depicted in a pre-formed state subsequent to being laser cut from a flat sheet or sheet material of, for example, super elastic material, such as Nitinol. As such, the occluder portion 24 and the anchor portion 26, in the pre-formed state, may be substantially planar and flat, after which, the frame components of the occluder portion 24 and/or the anchor portion 26 may then be heat-set to a desired shape and configuration, as known to one of ordinary skill in the art, similar to the fully deployed configuration (see FIG. 2). Further, as known to one of ordinary skill in the art, other processes may be employed, such as chemical etching and electro-polishing of the frame components. The occluder portion 24 may include ten face struts 50 and ten base extensions 48 with ten occluder eyelets 62 extending from the occluder zig-zag portion 52. Similarly, the anchor portion 26 may include ten anchor actuator arms 68 with ten anchor eyelets 80 extending from the anchor zig-zag portion 70. It should be noted that the occluder portion 24 and anchor portion 26 may include more or less frame components, such as the respective face struts 50 and anchor actuator arms 68, as known to one of ordinary skill in the art. As shown by dotted line 84, occluder eyelets 62 may be configured to couple to corresponding anchor eyelets 80 with a hinge-like coupling arrangement. Such may be employed by directly interlocking the occluder eyelets 62 with the anchor eyelets 80, as depicted in FIG. 2.

In another embodiment, the frame components of the occluder portion 24 and the anchor portion 26 may be laser cut from tubular material, rather than a flat sheet. In this embodiment, the frame components may be laser cut, and then heat set to the desired configuration, similar to that shown in FIG. 2. Various frame components of the occluder portion 24 and the anchor portion 26 may need to be modified as readily understood by one of ordinary skill in the art.

Figure 3B:
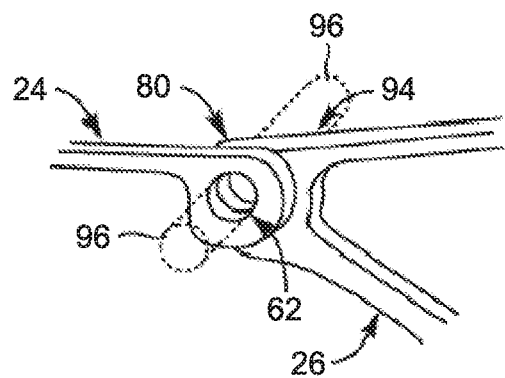
FIG. 3B is an enlarged view of a hinged coupling between the occluder portion and the anchor portion of the medical tool, according to another embodiment of the present invention.

With reference to FIG. 3B, in another embodiment, the occluder portion 24 and the anchor portion 26 may be hingably coupled together by aligning the occluder eyelets 62 with the anchor eyelets 80 and positioning an individual interlocking piece 94 (shown in outline) within and through each of the respective aligned eyelets 62, 80. Such an interlocking piece 94 may be a polymeric filament or the like. Ends 96 of the interlocking piece 94 may be heated to form a bulbous shape (not shown) at the ends 96 that, upon cooling, harden and maintain the bulbous shape so as to prevent the respective aligned eyelets from de-coupling. In this manner, the occluder and anchor eyelets 62, 80 may be interlocked via the interlocking piece 94 to provide a hinged coupling arrangement for the anchor portion 26 to pivot relative to the occluder portion 24 and, more particularly, for the anchor portion 26 to pivot about the occluder eyelets 62. In another embodiment, the interlocking piece 94 may be a metallic rivet press fitted through aligned eyelets to provide a hinged coupling arrangement.

Figure 4:
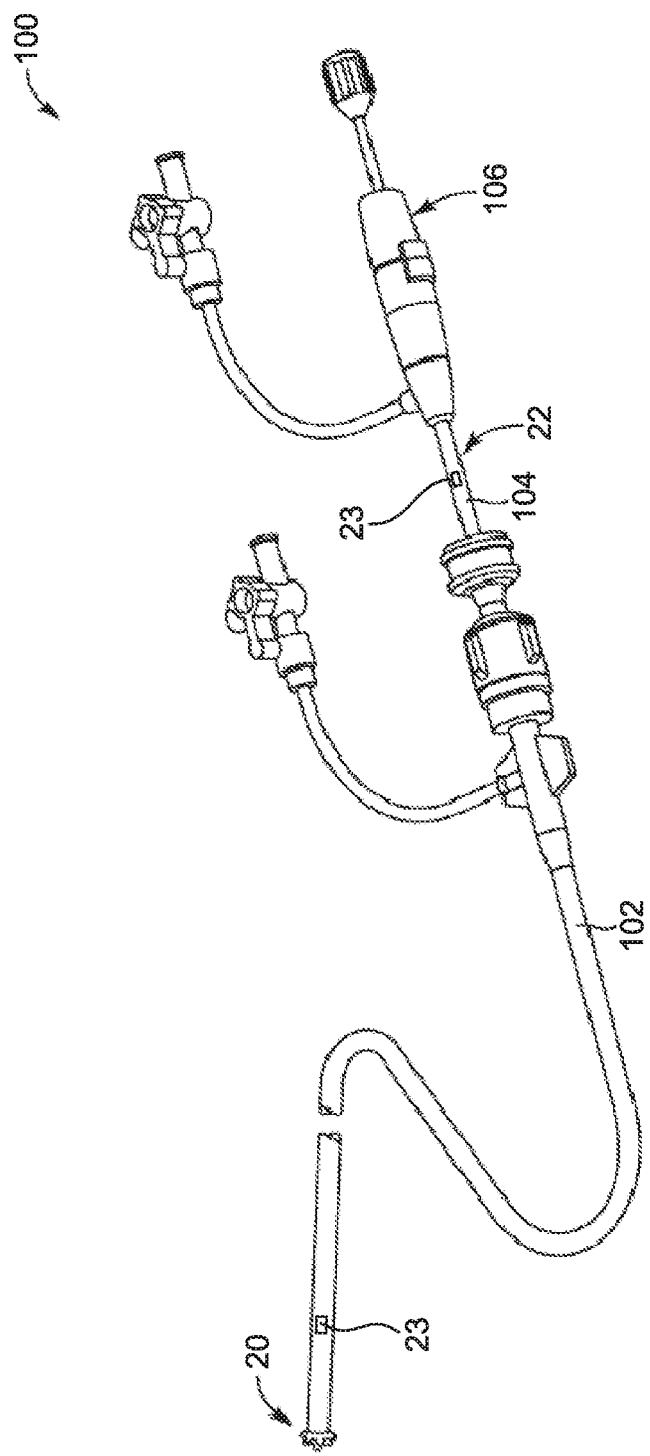
FIG. 4 is a perspective view of a medical tool delivery system, according to another embodiment of the present invention.

Now with reference to FIG. 4, a medical tool delivery system 100 for delivering the medical tool 20 to, for example, the LAA is provided. The medical tool delivery system 100 may include the before-mentioned delivery system 22, the medical tool 20, and a sheath 102. The delivery system 22 may include a delivery catheter 104 coupled to a handle 106 with the medical tool 20 operatively coupled to the handle 106 at a distal end of the delivery catheter 104. The delivery catheter 104 may be sized and configured to be inserted through the sheath 102 such that the medical tool 20 may be pushed through the sheath 102 to the distal end thereof. At least one sensor 23 may be located on the distal end of the sheath 102. The medical tool 20 may be partially exposed, at certain stages of delivery, as depicted. The functionality and detail of the various components of the medical tool delivery system 100 will be described in detail hereafter.

Figure 5:
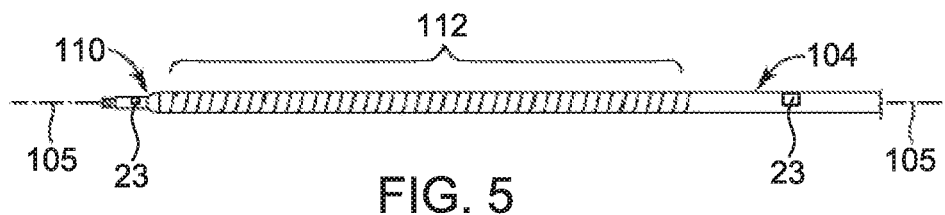
FIG. 5 is a side view of an end portion of a delivery catheter, according to another embodiment of the present invention.
Figure 5A:
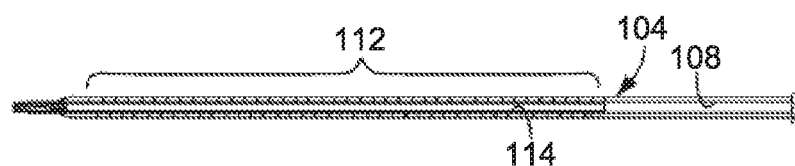
FIG. 5A is a cross-sectional view of the end portion of the delivery catheter, taken along a longitudinal axis of the delivery catheter of FIG. 5, according to another embodiment of the present invention.
Figure 5B:
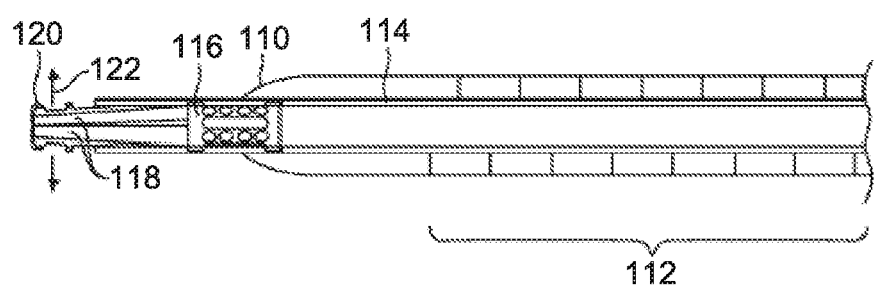
FIG. 5B is an enlarged view of the end portion of the delivery catheter, according to another embodiment of the present invention.

With reference now to FIGS. 5, 5A, and 5B, a distal portion of the delivery catheter 104 will now be described, FIG. 5A being a cross-sectional view of the distal portion of the delivery catheter 104 along an axis 106 thereof depicted in FIG. 5 and FIG. 5B being an enlarged cross-sectional view of a portion of the same. The delivery catheter 104 may define a lumen 108 extending longitudinally therethrough between a proximal end (not shown) and a distal end 110 of the delivery catheter 104. In one embodiment, the delivery catheter 104 may include a shaft (not shown), a spiral cut portion 112, an inner distal tube 114, and a collet 116. The distal portion of the delivery catheter 104 may include at least one sensor 23. Additionally or alternatively, a proximal portion of the delivery catheter 104 may include at least one sensor 23. Such distal portion of the delivery catheter 104 may include enhanced lateral flexibility along the region of the spiral cut portion 112. That is, the distal portion of the delivery catheter 104 may be more flexible than portions of the delivery catheter 104 more proximal than the spiral cut portion 112. The spiral cut portion 112 may be formed by spirally or helically cutting a slit into the peripheral structure of the distal portion of the delivery catheter 104, as depicted. The inner distal tube 114 may be coupled to the delivery catheter 104 and within the lumen 108 of the distal portion of the delivery catheter 104. The collet 116 may be positioned and thermally coupled to the distal end 110 of the delivery catheter 104 and within the inner distal tube 114 with collet fingers 118 extending distally therefrom. The collet fingers 118 may be sized and configured to latch to the hub of the medical tool (not shown) with nubs 120 or protrusions extending from free ends of the collet fingers 118. The collet fingers 118 are moveable outward, as indicated by arrows 122, and are biased to an inward position as shown. The collet 116 and collet fingers 118 may be made from a metallic material, such as stainless steel or Nitinol, or any other suitable metallic material that can maintain a biasing force. Such inward biasing of the collet fingers 118 will be discussed in further detail hereafter. With respect to the enhanced flexibility of the delivery catheter 104 along the spiral cut portion 112, such enhanced flexibility facilitates the medical tool to self-center upon being deployed in the LAA. In other words, the radial strength of the medical tool (not shown) may be greater than the lateral forces of the delivery catheter 104 along the spiral cut portion 112 to, thereby, allow the medical tool to self-center in the LAA in instances where the axis 106 of delivery catheter cannot be made concentric to the ostium of the LAA during delivery and deployment of the medical tool.

Figure 6A:
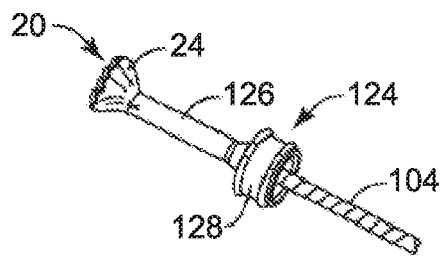
FIGS. 6A-6C are perspective views of a loader, depicting the loader being pushed over an occluder portion of the medical tool, the medical tool inserted into a sheath, and pushed to a distal end of the sheath, respectively, according to another embodiment of the present invention.
Figure 6B:
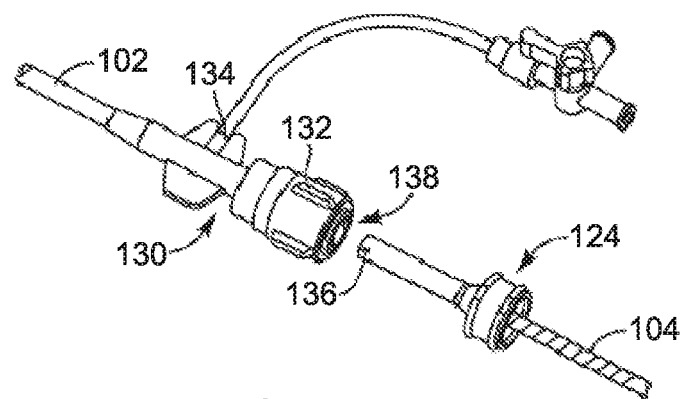
Figure 6C:
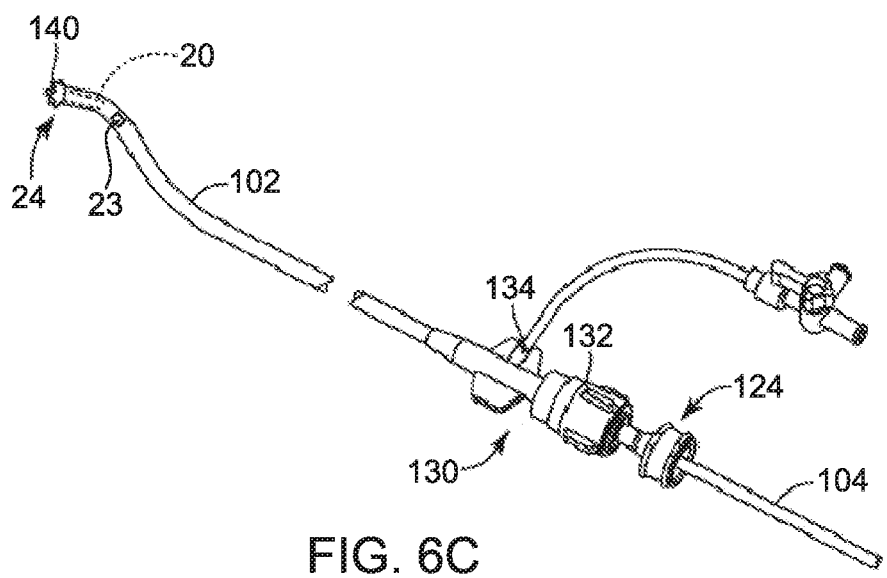
Figure 8:
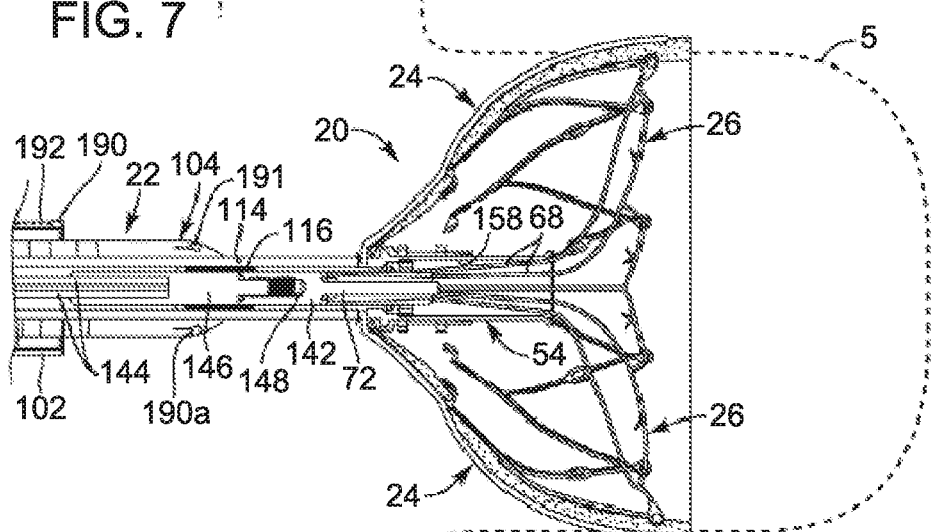
FIG. 8 is a cross-sectional side view of the distal portion of the delivery system and the medical tool, depicting a sheath withdrawn to deploy the occluder portion of the medical tool in the LAA and depicting the anchor portion in an anchor non-deployed position, according to another embodiment of the present invention.
Figure 8A:
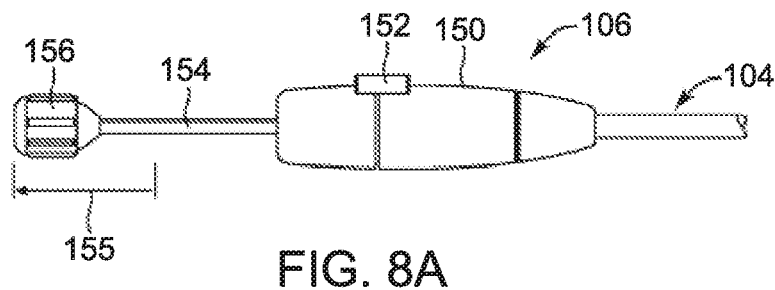
FIG. 8A is a side view of a handle, depicting the handle in a first position corresponding to the anchor non-deployed position, according to another embodiment of the present invention.

Now with reference to FIGS. 6A, 6B, and 6C, description of steps that may be employed for loading the medical tool 20 into the sheath 102 will now be provided. For example, the delivery catheter 104 may include a loader 124 sized and configured to facilitate loading the occluder portion 24 of the medical tool 20 into the sheath 102 so that the delivery catheter 104 can push the occluder portion 24 through the sheath 102 to a distal portion thereof. With reference to FIG. 6A, the loader 124 may include a tube portion 126 and a handle portion 128. The loader 124 may be slideably positioned over the delivery catheter 104 such that the delivery catheter 104 extends through a bore defined through the loader 124. The loader 124 may be moved over the distal end of the delivery catheter 104 and manually moved or forced over the occluder portion 24 of the medical tool 20 so that occluder portion 24 moves to a constricted position enclosed within the tube portion 126. However, prior to moving the loader 124 over the occluder portion 24, the anchor portion should be in a non-deployed position such that an actuator knob and plunger shaft of the handle 106 should be moved to a proximal position, as depicted in FIGS. 8 and 8A. Referring back to FIG. 6A, once the loader 124 is moved completely over the occluder portion 24, the medical tool 20 may then be advanced through the sheath 102. The sheath 102, at this point, has already been advanced through the circulatory system to the heart with a distal portion of the sheath 102 positioned in the LAA (not shown), employing typical techniques known in the art.

As depicted in FIGS. 6B and 6C, the loader 124 may be inserted into the sheath 102 and, more particularly, a sheath hub 130. The sheath hub 130 may be coupled at a proximal end of the sheath 102. The components of the sheath hub 130 may include a valve 132 and a sheath fluid port 134. The valve 132 may be a rotating hemostasis valve, such as a Touhy Borst valve or the like, configured to constrict or limit back-flow of blood from the sheath 102 upon rotation of the valve 132. The sheath fluid port 134 may extend from the sheath hub 130 and may be sized and configured to flush or aspirate air from the sheath 102 that may become trapped upon loading the medical tool 20 into the sheath 102. In another embodiment, the loader 124 may also include a valve positioned around the delivery catheter 104 to maintain hemostasis while inserted into the sheath hub 130.

As set forth, the loader 124 may be mated or inserted into the sheath hub 130 with a snap or click fit via nubs 136 at the distal end of the tube portion 126 and a rib (not shown) within a bore 138 defined in the sheath hub 130. Once the loader 124 is positioned within the sheath hub 130, the delivery catheter 104 may be advanced through a lumen defined longitudinally in the sheath 102 such that the distal end of the delivery catheter 104 moves to a distal portion of the sheath 102 to expose a distal tip of the occluder portion 24 of the medical tool 20 from the distal end of the sheath 102. With this arrangement, the distal tip of the occluder portion 24 may be exposed at the distal end of the sheath 102 and provides, due to the occluder material, a cushioned tip 140, without any exposed metal frame members, facilitating an atraumatic entry into the LAA, thereby, reducing the potential of effusions in the LAA.

Referring to FIGS. 7 through 11, deployment and detachment of the medical tool 20 in an LAA 5 (shown in outline) relative to the delivery system 22 will now be described. With respect to FIGS. 7 and 8, upon the physician positioning the distal portion of the sheath 102 in the LAA 5 with the medical tool 20 positioned at the distal portion of the sheath 102 with the cushioned tip 140 of the occluder portion 24 exposed at the distal end of the sheath 102, the physician may atraumatically position the distal portion of the sheath 102 to a desired location in the LAA 5. Once the desired location is determined, the physician can deploy the occluder portion 24 of the medical tool 20. Such may be employed by simply withdrawing the sheath 102 or manually moving the sheath 102 in a proximal direction. As the sheath 102 is withdrawn, the occluder portion 24 self-expands to an occluder deployed position with the anchor portion 26 maintained in an anchor non-deployed position, as depicted in FIG. 8.

With respect to FIG. 8, a distal portion of the delivery catheter 104 coupled to the medical tool 20 is shown. The delivery catheter 104 of this embodiment is coupled to the medical tool 20 with an occluder hub nut 142 and collet 116 arrangement. For example, the distal portion of the delivery catheter 104 includes the inner distal tube 114 and an actuator shaft 144. The actuator shaft 144 may include a layered coil, such as a speedometer cable, at a distal end portion thereof, which may be coupled to an inner distal connector 146 moveable within the collet 116. As previously set forth, the collet 116 may include collet fingers 118 extending distally from the collet 116. The inner distal connector 146 may include threads sized and configured to couple to the occluder hub nut 142 and, more particularly, to a threaded screw hole 148 defined in the occluder hub nut 142. The occluder hub nut 142, at a distal end thereof, may include the splined sleeve 72. As previously set forth, the splined sleeve 72 may be sized and configured to couple end portions of each of the anchor actuator arms 68. In another embodiment, the inner distal connector 146 and occluder hub nut 142 may be reversed such that the inner distal connector 146 includes a nut configuration and the occluder hub nut 142 includes a screw configuration. In either case, the medical tool 20 may be threadably coupled to the delivery catheter 104.

With reference to FIG. 8A, one embodiment of the handle 106 is depicted. The handle 106 may include a handle housing 150, an anchor actuator release button 152, a plunger shaft 154, and an actuator knob 156. The handle housing 150 may be coupled to a proximal portion of the delivery catheter 104. The plunger shaft 154 and actuator knob 156 is shown in a first position that correlates to the anchor portion 26 being in a non-deployed position (see FIG. 8). The plunger shaft 154 and actuator knob 156 may be moved bi-linearly between a first position and a second position while depressing the anchor actuator release button 152. The functions and various components of the handle 106 will become apparent to one of ordinary skill in the art as discussed in further detail hereafter.

As depicted in FIGS. 8 and 8A, the anchor portion 26 of the medical tool 20 is in an anchor non-deployed position. The actuator knob 156 and plunger shaft 154 are moved to the first position, as indicated by arrow 155 that corresponds to the anchor non-deployed position prior to loading the medical tool 20 into the loader 124 and then into the sheath 102 (see FIGS. 6A and 6B). In the anchor non-deployed position, the inner distal connector 146 is threadably coupled to the occluder hub nut 142 and is positioned proximal the hub 54 with the anchor portion 26 in a first position or an anchors non-deployed position or, otherwise said, an anchors-in position with a portion of the anchor actuator arms 68 proximal the hub 54 and within a bore 158 defined in the hub 54. Further, in the anchor non-deployed position, the plunger shaft 154 and knob 156 of the handle 106 may be in a proximal or first position as well. With this arrangement, a physician may determine the most favorable position of the medical tool 20 within the LAA 5 with the occluder portion 24 in the deployed position prior to deploying the anchor portion 26.

Figure 9:
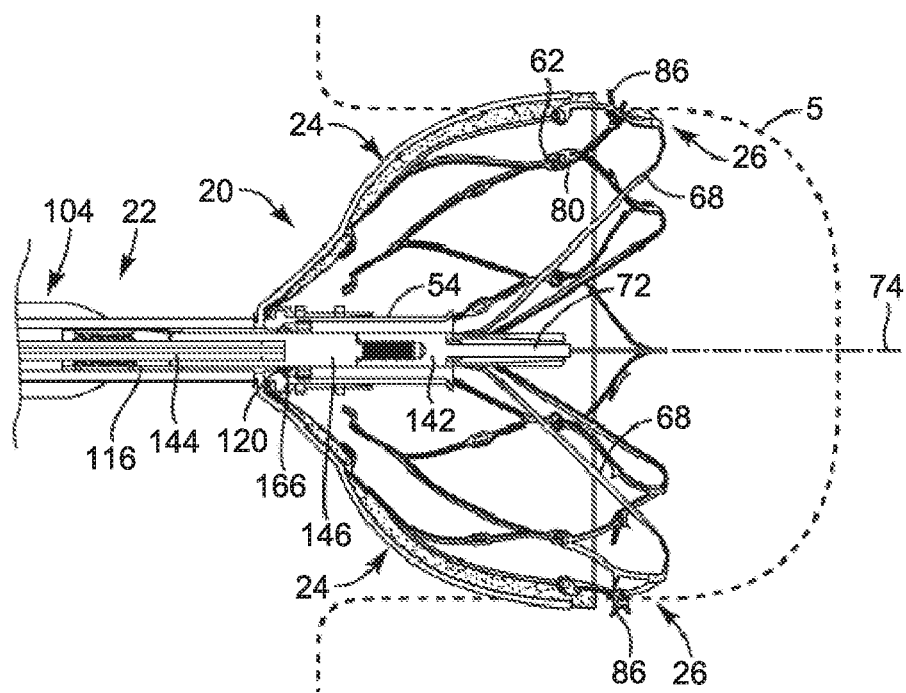
FIG. 9 is a cross-sectional side view of the distal portion of the delivery system and the medical tool, depicting both the occluder portion and the anchor portion in an anchor deployed position in the LAA, according to another embodiment of the present invention.
Figure 9A:
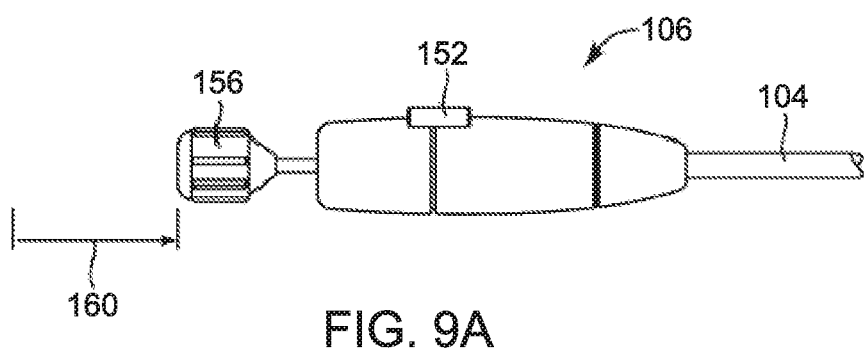
FIG. 9A is a side view of the handle, depicting the handle in a second position corresponding to the anchor deployed position, according to another embodiment of the present invention.

Now turning to FIGS. 9 and 9A, the anchor portion 26 of the medical tool 20 may be moved to an anchor deployed position or anchor-out or anchor second position once the physician determines the deployed occluder portion 24 is positioned in the LAA 5 as desired. Such anchor deployed position may be employed by manually moving the actuator knob 156 distally, as indicated by arrow 160, while also depressing the release button 152. In the anchor deployed position, the inner distal connector 146 and occluder hub nut 142 are also moved distally from the collet 116 and into the hub 54 or through the hub 54. Such linear distal movement also moves the anchor actuator arms 68, coupled to the splined sleeve 72, from a distal portion of the delivery catheter 104, through and out of the hub 54 to an everted, deployed position or an expanded position such that the anchor portion 26 unfolds and expands radially by pivoting or rotating at the hinged connection (i.e., at occluder and anchor eyelets 62, 80) between the occluder portion 24 and anchor portion 26. At the anchor deployed position, hooks 86 or tines of the anchor portion 26 are sized and configured to grab tissue and prevent movement so as to effectively anchor the medical tool 20 within the LAA 5. Additionally or alternatively, the hooks 86 or tines of the anchor portion 26 are sized and configured to grab tissue and prevent movement so as to effectively anchor the medical tool 20 within the left atrium. Once the anchor portion 26 is deployed, the physician may view the medical tool 20 through imaging techniques to ensure proper positioning of the medical tool 20 in the LAA 5 while also performing stability tests by pulling proximally on the handle 106 to ensure the medical tool 20 is effectively engaging the LAA 5. Such imaging techniques may be enhanced by markers strategically located on the medical tool 20 and delivery catheter 104 to provide imaging information to the physician. Such markers may be made from a radiopaque material, such as platinum, gold, tantalum, or alloys thereof, or any other suitable radiopaque materials that are biocompatible.

The hooks 86 of the anchor portion 26 may extend both distally and proximally so as to substantially prevent movement of the medical tool 20 in both the proximal and distal directions relative to the LAA 5. In one embodiment, the hooks 86 may include an acute angle 88 (FIG. 3A) relative to the axis 74 of the medical tool 20 or the struts of the anchor zig-zag portion 70. The hooks 86 are configured to grab and may dig at the tissue of the LAA 5. Such hooks 86 may be sized, oriented, and configured to prevent puncture or piercing of the hooks 86 all the way through the tissue of the LAA 5, but provide effective and even aggressive engagement with the tissue to provide safe anchoring of the medical tool 20 in the LAA 5.

If the physician is dissatisfied with the location or engagement of the medical tool in the LAA, the physician may readily disengage the anchor portion 26 from the tissue of the LAA by simply moving the actuator knob 156 in the proximal direction to the first position (FIG. 8A), which simultaneously moves the actuator shaft 144 proximally and, thus, pivots the anchor portion 26 to a disengaged or anchor non-deployed position. The physician may then re-position the occluder portion 24 within the LAA 5 and, once satisfied with the location of the occluder portion 24 in the LAA 5, the physician may readily move the actuator knob 156 forward or a distal direction to pivot and re-engage the anchor portion 26 with the tissue of the LAA 5. The physician may then determine again through imaging and stability tests if the medical tool 20 is positioned in the LAA 5 in an effective and safe manner that satisfies the physician. As can be readily understood, the steps of re-positioning the occluder portion 24 and re-engaging the anchor portion 26 of the medical tool 20 can be repeated until the physician is satisfied.

Figure 10:
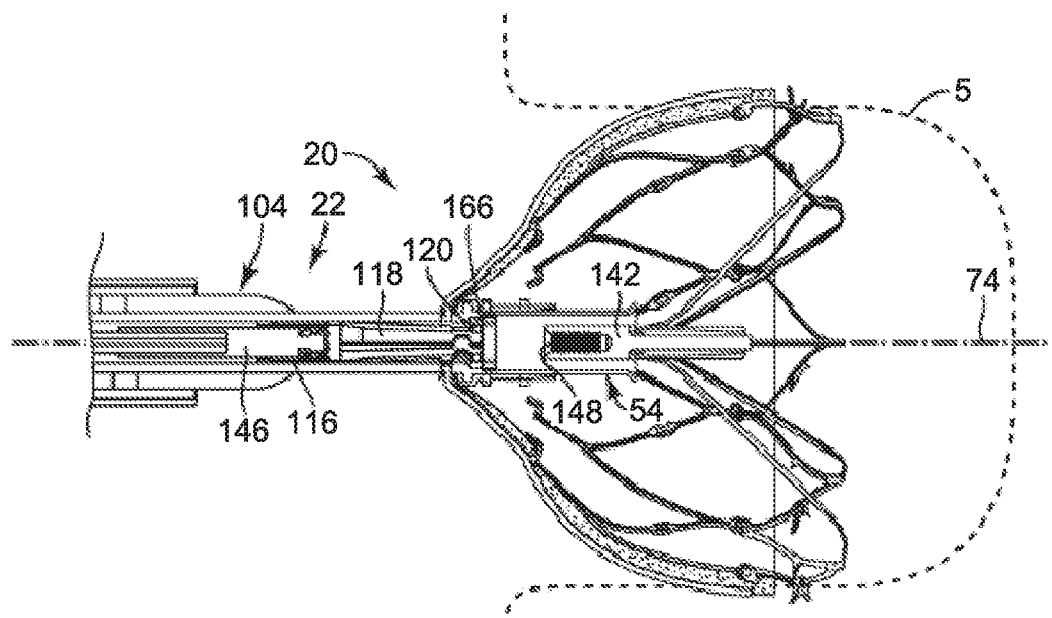
FIG. 10 is a cross-sectional side view of the distal portion of the delivery system and the medical tool, depicting the delivery system in the process of being released from the medical tool in the LAA, according to another embodiment of the present invention.
Figure 10A:
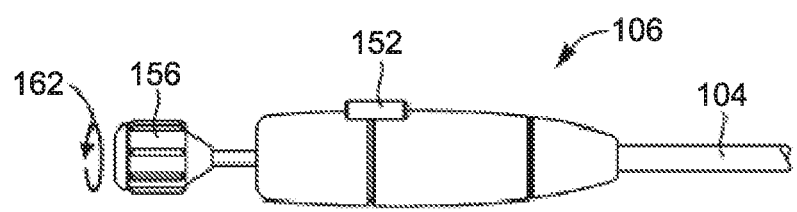
FIG. 10A is a side view of the handle, depicting a portion of the handle being rotated for releasing the medical tool, according to an embodiment of the present invention.
Figure 10B:
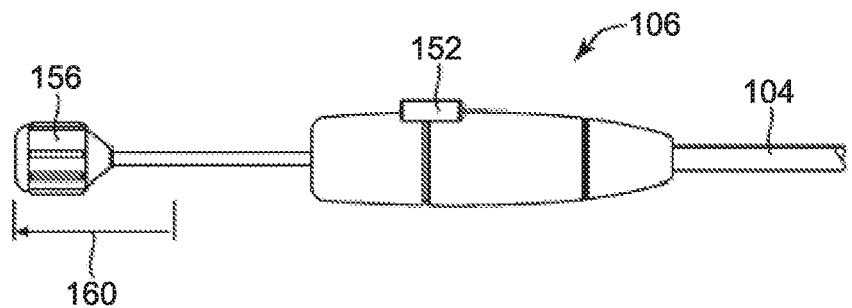
FIG. 10B is a side view of the handle, depicting a portion of the handle actuated from the second position to the first position, according to an embodiment of the present invention.
Figure 11:
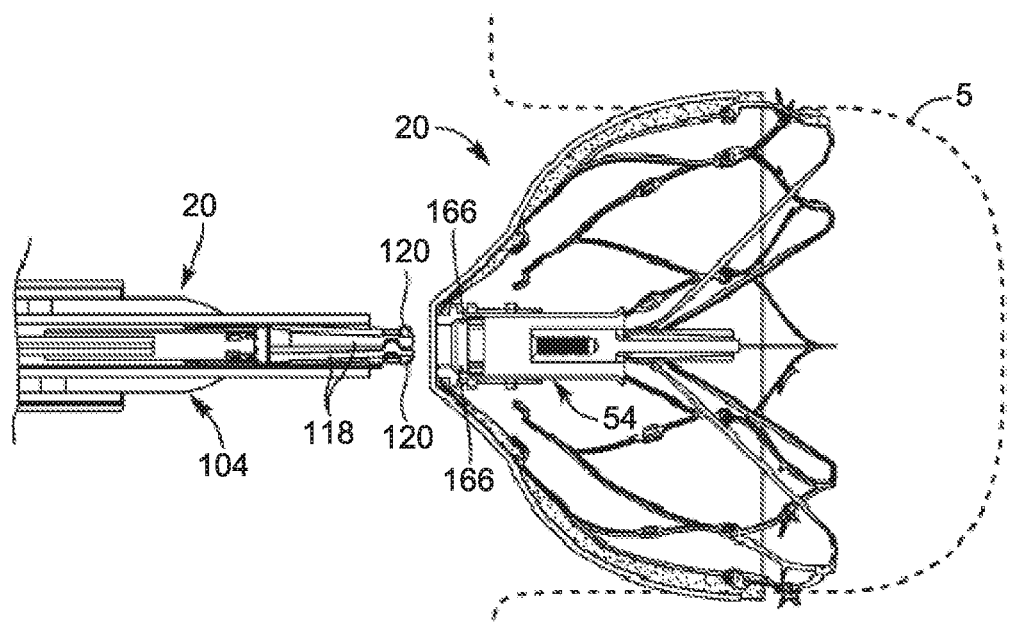
FIG. 11 is a cross-sectional side view of the distal portion of the delivery system and the medical tool, depicting the delivery catheter fully released from the medical tool, according to another embodiment of the present invention.

Now referring to FIGS. 10, 10A, and 10B, the functions of releasing the medical tool 20 will now be described. The medical tool 20 may be detached or released by unscrewing the inner distal connector 146 from the screw hole 148 defined in the occluder hub nut 142. Such releasing may be employed by rotating the actuator knob 156 of the handle 106 counter-clockwise several turns, as indicated by arrow 162, until the inner distal connector 146 unwinds from the screw hole 148 of the occluder hub nut 142. The actuator knob 156 may then be pulled proximally back to the first position, as indicated by arrow 164, while depressing the release button 152, which facilitates movement of the inner distal connector 146 in the proximal direction. As the inner distal connector 146 is moved proximally through or into the collet 116, the collet fingers 118 extending distally from the collet 116 collapse inward since the collet fingers 118 may be biased toward an inward position. In other words, prior to the inner distal connector 146 being unwound, the collet fingers 118 may be held in an outer position substantially concentric with the axis 74 of the medical tool 20, which maintains the delivery catheter 104 locked to the medical tool 20. The collet fingers 118 include outward extending nubs 120 that are held against an abutment 166 within the hub 54 (also shown in FIG. 9). In this manner, once the inner distal connector 146 is unscrewed from the occluder hub nut 142 and moved to a proximal position away from the collet fingers 118, the collet fingers 118 flexibly collapse with a bias to an inward position to move the nubs 120 away from the abutment 166 in the hub 54, thereby, unlocking or unlatching the delivery catheter 104 from the medical tool 20. The delivery catheter 104 may then be removed from the medical tool 20 with the collet fingers 118 collapsed and the nubs 120 moved proximally from the abutment 166 within the hub 54 as depicted in FIG. 11.

Figure 12:
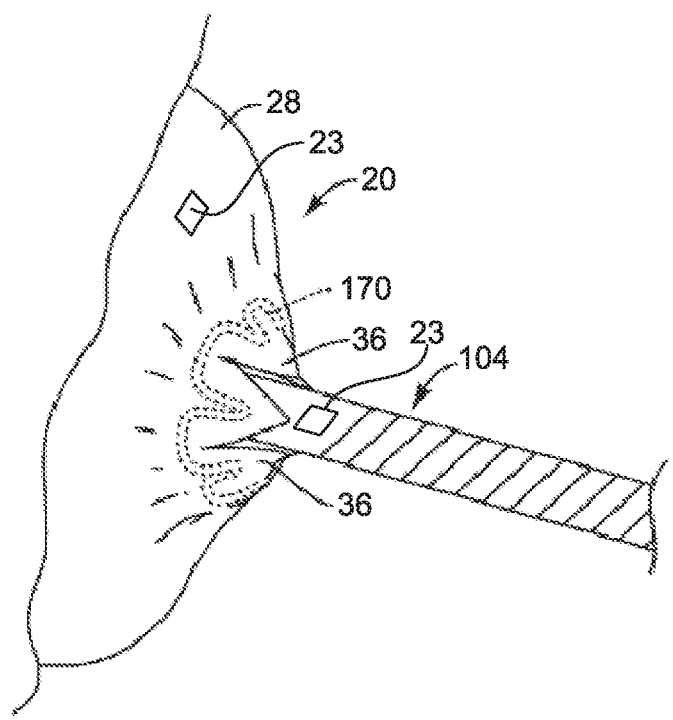
FIG. 12 is a partial perspective view of the proximal side of the medical tool coupled to the delivery system, according to another embodiment of the present invention.

With respect to FIGS. 2 and 12, a moveable portion that may include a spring 170 is depicted. In one embodiment, the moveable portion may include a spring 170 with a polymeric covering in the form of polymeric flaps or occluder flaps 36. Such moveable portion having the spring 170 may be sized and configured to close-off the bore 158 of the hub 54 once the delivery catheter 104 is released from the medical tool 20. The spring 170 may include a clover configuration or any other suitable configuration to effectively close-off the hub 54. The spring 170 may move between a first biased position (or open first position) and a second relaxed position (or closed second position). The first biased position of the spring 170 (shown in outline form) is depicted in FIG. 12, which is the position of the spring 170 with the delivery catheter 104 coupled to the hub 54. In one embodiment, the position of the delivery catheter 104 attached to the hub 54 holds the spring 170 in the biased or open first position. Once the delivery catheter 104 is removed from the hub 54, the spring 170 may automatically move to the closed, second relaxed position (see FIG. 2) with the occluder flaps 36 (see also FIG. 1) substantially minimizing or eliminating any through hole on the proximal face and adjacent the hub 54. In the second relaxed position of the spring 170, the bore 158 defined in the hub 54 is substantially closed-off with occluder flaps 36, leaving only a cross-like slit (as depicted by adjacently extending occluder flaps 36 in FIG. 1) and substantially eliminating any metal exposed at the hub 54. In this manner, the occluder flaps 36, in the closed second position, advantageously provides a surface at the proximal face of the device without exposed metal at the hub 54 and, further, provides a contiguous surface with the polymeric material of the occluder portion 24 that closes off the hub 54.

As previously set forth, the spring 170 may be embedded in the occluder material or tissue growth member 28 or attached to an inner occluder material surface such that the spring 170 may include various layers and/or folds of, for example, ePTFE, with one or more slits defining the flaps 36 that facilitates interconnection of the delivery catheter 104 to the hub 54 when the spring 170 is in the first biased position but then may substantially close-off the bore 158 defined in the hub 54 when in the second relaxed position. Such arrangement is advantageous to substantially prevent blood flow through the hub 54 or to substantially prevent the potential of migrating emboli or thrombus from the hub 54 itself once the medical tool 20 is positioned in the LAA. In this manner, the spring 170 facilitates closing-off the through hole of the hub 54 and/or covers any exposed metal at the hub so that emboli or thrombus that may collect on the metal is prevented from escaping from the hub. In other words, the flaps 36 provide a substantially impassible barrier relative to otherwise potential migrating emboli or thrombus at the hub 54.

Figure 13A:
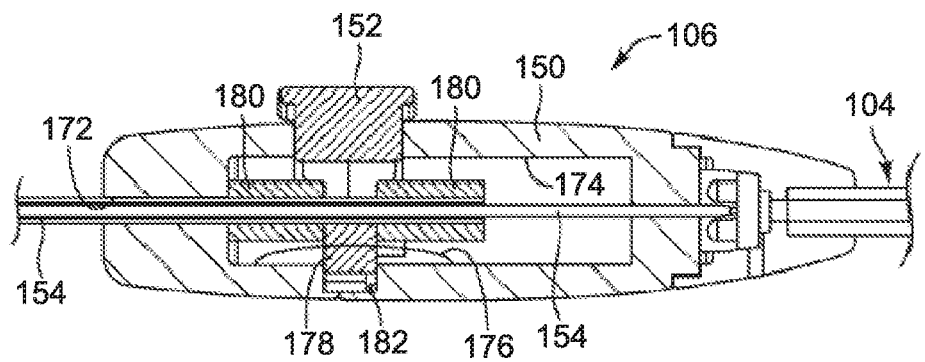
FIGS. 13A and 13B are cross-sectional side views of the handle, depicting a release button in a first and second position, respectively, to facilitate actuation of a plunger shaft, according to another embodiment of the present invention.
Figure 13B:
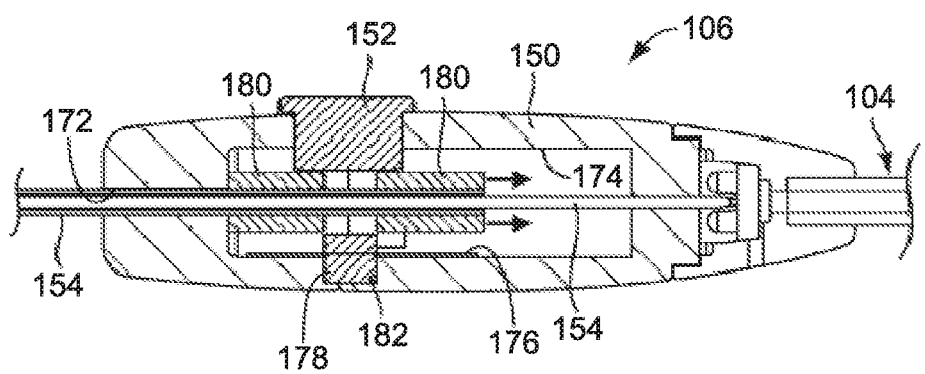

Now referring to FIGS. 13A and 13B, actuation of the release button 152 of the handle 106 is depicted. The handle housing 150 defines a hole 172 that may extend along a longitudinal axis of the handle housing 150 and may be sized to hold the plunger shaft 154 to move bi-linearly therethrough. The handle housing 150 may also define a hollow portion 174 therein. The plunger shaft 154 may extend through the handle housing 150 and be coupled to components coupled to actuator shaft 144 and the inner distal connector 146 at the distal portion of the delivery catheter 104 (see FIG. 9). The handle 106 also may include a leaf spring 176 configured to bias against the release button 152. The release button 152 may include a button post 178. The leaf spring 176 may be coupled to the button post 178 to bias the release button 152 to a non-depressed position or first position. The plunger shaft 154 may also include two travel stops 180 fixed thereto. By depressing the release button 152 to a depressed position or second position, the button post 178 depresses the leaf spring 176 and moves within a cavity 182. Once the button post 178 is moved within the cavity 182, the travel stops 180 coupled to the plunger shaft 154 may then freely move distally (and then back proximally) past the button post 178 a predetermined distance gauged by the travel stops 180 within the hollow portion 174 defined by the handle housing 150. In this manner, the plunger shaft 154 may move the predetermined distance which directly corresponds with the distance or length moved by the actuator shaft 144 and actuation of the anchor portion of the medical tool 20 between the anchor non-deployed position and anchor deployed position (see FIGS. 8 and 9).

Referring back to FIG. 8, in another embodiment, the sheath 102 may include an imaging device 190. The imaging device 190 may be sized and configured to be positioned at a distal end of the sheath 102 and may include one or more lines 192 extending from the imaging device 190 and proximally toward the sheath hub 130 (FIG. 5C) for transferring imaging information from the imaging device 190 to a computer and a display (not shown), as known to one of ordinary skill in the art, and viewable by the physician in real-time. The sheath 102, upon being withdrawn from the occluder portion 24, being positioned substantially concentric or proximal of the medical tool 20, may be at a vantage point and location in the left atrium adjacent the LAA to provide detailed imaging information otherwise not readily available to the physician. The imaging device 190 may be an ultrasound imaging device or any other suitable imaging device known in the art. In another embodiment, an imaging device 190a may be positioned proximal a distal end of the delivery catheter 104 in a similar manner to that described above. In still another embodiment, the distal end of the delivery catheter 104 and/or sheath 102 may include one or more positioning sensors 191. The positioning sensors 191 may be configured to sense pressure, flow, and any other cardiac dynamics that may be useful to the physician. In this manner, the positioning sensors 191 and/or imaging device 190, may provide additional information to assist the physician to accurately position the medical tool 20 in the LAA 5.

Now with reference to FIGS. 14A and 14B, another embodiment of a medical tool 200 coupled to a distal portion of a delivery catheter 202, the medical tool 200 (depicted in a simplistic profile view) in a partially deployed position and fully deployed position, respectively, is provided. As in previous embodiments, the medical tool 200 may include an occluder portion 204 and an anchor portion 206 that may be separately deployed. For example, once a sheath 208 is positioned in the LAA (not shown) with the medical tool 200 at a distal end portion thereof, the sheath 208 is withdrawn to deploy an occluder portion 204 of the medical tool 200 or to partially deploy the medical tool 200. Once the occluder portion 204 is deployed, then the anchor portion 206 may be deployed, to fully deploy the medical tool 200.

In this embodiment, the occluder portion 204 is substantially similar to the previous embodiment, except the tissue growth member 210 is attached to an outer surface of the frame components of the occluder portion 204. The tissue growth member 210 of this embodiment may include similar layering of one or more materials as set forth for the tissue growth member described in detail relative to FIG. 1B. Further, although the anchor portion 206 may be hingably coupled to the occluder portion 204 with a hinge arrangement 212 and, in many respects functions similar to the previous embodiment, the anchor portion 206 of this embodiment includes multiple separate and distinct anchor frame segments 214, best shown in FIG. 15.

With reference to FIG. 15, the frame components of the occluder portion 204 and the anchor portion 206 are depicted in, for example, a preformed state subsequent to being laser cut from a flat sheet of super elastic material, such as Nitinol. For simplicity purposes, there is only one anchor frame segment 214 shown, but in this embodiment, there may be five anchor frame segments 214 to correspond and couple to, for example, occluder frame apertures 216 of the occluder portion 204. As shown, the frame components of the occluder portion 204 may be substantially similar to the frame components of the occluder portion 204 described in the previous embodiment relative to FIG. 3.

With respect to the anchor frame segments 214, each anchor frame segment 214 may extend between a first end 218 and second end 220 with two actuator arms 222 extending therebetween such that each anchor frame segment 214 may exhibit a "Y" or "V" configuration in the pre-formed state. Each actuator arm 222 may include an anchor hinge aperture 224 at the second end 220 and, at the first end 218, the actuator arm 222 may be coupled to a collar arrangement 226 or splined sleeve, similar to that of the previous embodiment. With this arrangement, the actuator arms 222, as depicted in FIGS. 14A and 14B, may pivot about the occluder portion 204 at the hinge arrangement 212. Further, the actuator arms 222 may form a loop configuration or loop extension in the anchor deployed position with the first end 218 of the actuator arms 222 moveable or actuatable through the hub 228 of the medical tool 200.

Figure 7:
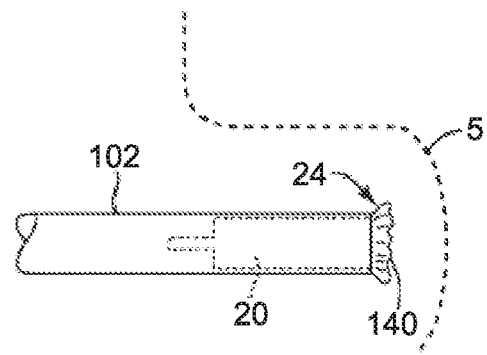
FIG. 7 is a side view of a distal portion of the sheath, depicting a portion of the medical tool exposed at a distal end of the sheath in the LAA, according to another embodiment of the present invention.

Now with reference to FIGS. 16A, 16B, and 17, another embodiment of a medical tool 250 depicted in a partially deployed position (FIG. 16A) and a fully deployed position (FIG. 16B), similar to previous embodiments, is depicted. In this embodiment, the occluder portion 252 can be similar to the previous embodiments, but the anchor portion 254 may include an anchor zig-zag portion 256 and loop extensions 258 or actuator arms as separate anchor frame components. In this embodiment, the medical tool 250 may include a dual hinge arrangement. For example, the occluder portion 252 may be hingably coupled to an anchor zig-zag portion 256 with a first hinge arrangement 260 and the anchor zig-zag portion 256 may be hingably coupled to the loop extensions 258 with a second hinge arrangement 262. The profile and functionality of the medical tool 250 may be similar to the previous embodiments, except the loop extensions 258 may take a more direct inward angle from the anchor zig-zag portion 256 due to the second hinge arrangement 262 therebetween. Similar to the embodiment of FIG. 15, this embodiment may include ten loop extensions 258 or actuator arms, though for simplicity purposes only two loop extensions 258 (as a single loop extension segment) are shown in FIG. 17. It should be noted that the embodiments of FIGS. 14 and 16 also provide the feature to facilitate a cushion tip (not shown) as depicted in FIG. 7 when constricted in the sheath 264. Further, it should be noted the embodiments depicted and described relative to FIGS. 1, 14 and 16 include similar features and structure and, therefore, the descriptions provided in one embodiment may also be applicable to the other described embodiments.

Figure 19:
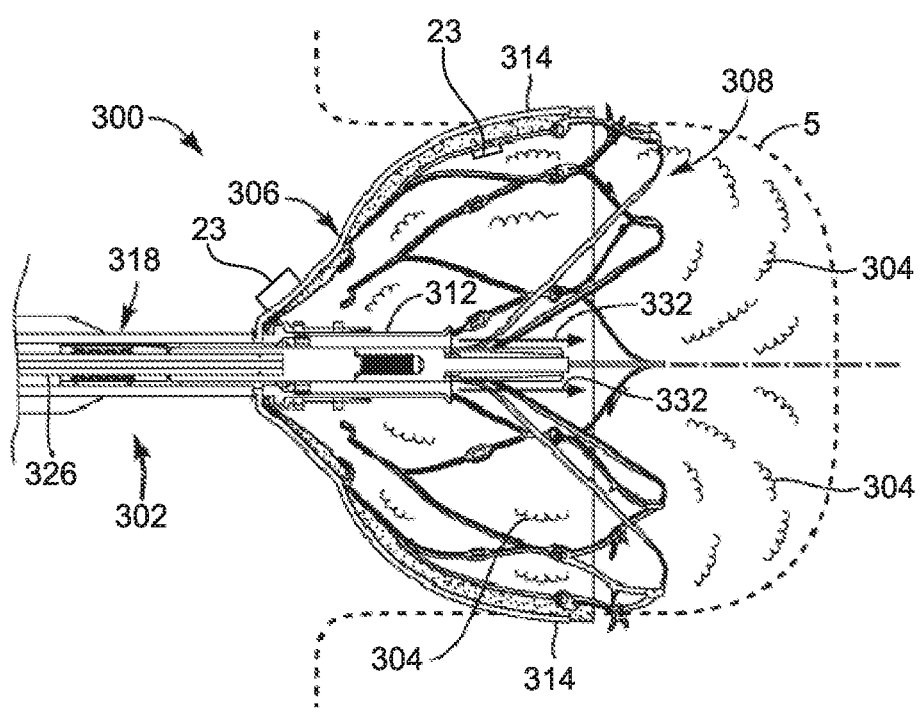
FIG. 19 is a cross-sectional view of the medical tool and the distal portion of the delivery system, depicting a fluid flowing from a hub of the medical tool and into the left atrial appendage, according to another embodiment of the present invention.
Figure 20:
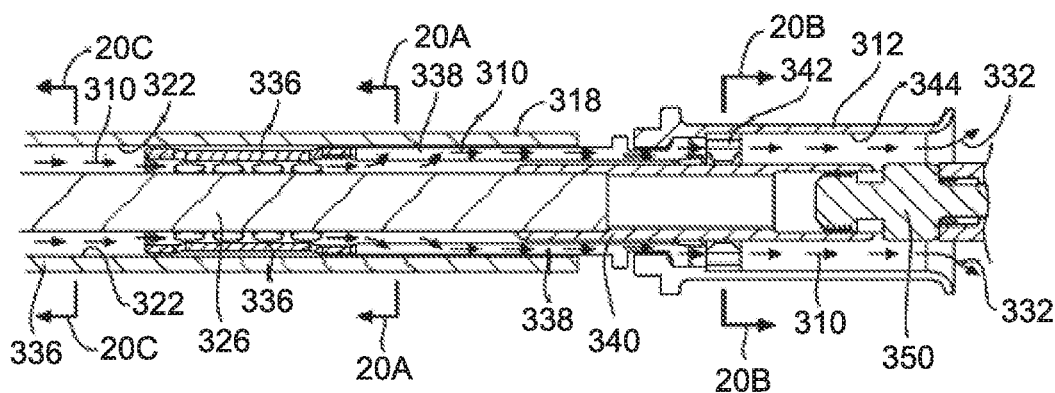
FIG. 20 is an enlarged cross-sectional view of the distal portion of the delivery system and the hub of the medical tool (with the occluder portion removed for simplification purposes), depicting a flow path of the fluid moving through the delivery system and hub of the medical tool, according to another embodiment of the present invention.

Now with reference to FIGS. 18 through 20, another embodiment of a medical tool 300 and a medical tool delivery system 302 for modifying an LAA 5 of the heart is provided. In this embodiment, the structural components and functionality of the medical tool 300 and the medical tool delivery system 302 may be substantially similar to any one of the embodiments previously described. For example, the medical tool 300 may include an occluder portion 306 and an anchor portion 308, similar to that described above.

In this embodiment, upon the medical tool 300 being positioned within the LAA 5 with the anchor portion 308 deployed and engaged with tissue of the LAA 5, the medical tool delivery system 302 and the medical tool 300 may include a common flow path 310 defined therethrough for injecting a fluid 304 through a hub 312 of the medical tool 300 and to a distal side of the medical tool 300 and into the LAA 5. One important aspect of this embodiment may be that the occluder portion 306 of the medical tool includes a substantially non-permeable material of, for example, a polymeric material, such as foam and/or ePTFE, described in earlier embodiments herein as the tissue growth member. In one embodiment, the ePTFE may be the material that is non-permeable.

In one embodiment, the occluder portion 306 of the medical tool 300 may include a polymeric material, such as the before-described foam and/or ePTFE. In another embodiment, the polymeric material may include a bio-agent coated over or impregnated within the polymeric material. Such bio-agent may be configured to enhance tissue growth and endothelization over the proximal side of the occluder portion 306 of the medical tool 300. In another embodiment, the polymeric material may include a coating thereon that may be an anti-thrombotic coating, such as Heprin. In still another embodiment, the occluder portion may include a biological tissue, in addition to or instead of the before-described polymeric material. Such biological tissue may be a biological sourced tissue, such as pericardial tissue and/or peritoneum tissue, or any suitable biological tissue that is biocompatible as known in the art. Further, the biological tissue may be non-permeable, strong, and thin so as to readily be moved with the occluder portion frame structure between collapsed and expanded configurations. Further, the non-permeable characteristics of the pericardial tissue may function to substantially maintain fluid 304 in the LAA 5 upon the medical tool being positioned in the LAA. In another embodiment, the biological tissue may be permeable or include portions with permeable characteristics and other portions with non-permeable characteristics.

With reference to FIGS. 18, 18A and 18B, the medical tool delivery system 302 includes a sheath 316, a delivery catheter 318 coupled to a handle 320, and the medical tool 300 coupled to a distal end of the delivery catheter 318, similar to that described and depicted relative to FIG. 4 herein (as well as other embodiments herein). The delivery catheter 318 extends between a proximal end and a distal end such that the proximal end is coupled to the handle 320 and the distal end of the delivery catheter 318 is coupled to the implantable medical tool 300. Further, the delivery catheter 318 defines a lumen 322 extending along a longitudinal length of the delivery catheter 318. The handle 320 may include a fluid port 324 sized and configured to directly communicate with the lumen 322 of the delivery catheter 318. Also, the delivery catheter 318 may include an actuator shaft 326 (coupled to the handle 320 and actuatable by the actuator knob 321) extending therethrough for controlling actuation of the anchor portion 308 of the medical tool 300. With this arrangement, fluid, such as fluid 304, may be injected through the fluid port 324 of the handle 320 and directly through the lumen 322 of the delivery catheter 318 such that the fluid 304 may advance toward the medical tool 300. Further, the distal portion of the delivery catheter 318 may include at least one sensor 23. Additionally or alternatively, a proximal portion of the delivery catheter 318 may include at least one sensor 23.

As in previous embodiments, the delivery catheter 318 and the medical tool 300 coupled at the distal end thereof may be sized and configured to be pushed through a sheath lumen 317 defined along a length of the sheath 316. The sheath 316 may also include a sheath fluid port 328 sized and configured to inject fluid, such as fluid 304, through the sheath lumen 317 and to exit from the distal end of the sheath 316. Further, the distal portion of the sheath 316 may include at least one sensor 23.

The fluid, such as fluid 304, may be injected through the fluid port 324 of the handle 320, as well as the sheath fluid port 328 of the sheath 316, with an injection device 330. In one embodiment, the injection device 330 may be a syringe for manual injection through the fluid port 324 of the handle 320 or through the sheath fluid port 328 of the sheath 316. In another embodiment, the injection device 330 may include an injection machine that controls the pressure, amount, and/or flow rate of fluid being injected through the fluid port 324 of the handle 320 (or through the sheath fluid port 328 of the sheath 316), as known to one of ordinary skill in the art.

Now with reference to FIGS. 19 and 20, fluid, such as fluid 304, may flow through the lumen 322 of the delivery catheter 318, as discussed above, and through the hub 312 (and components associated therewith) of the medical tool 300, the medial device 300 being positioned in the LAA 5. As the fluid 304 exits the hub 312 of the medical tool 300, as depicted by arrows 332 in FIG. 19, the fluid 304 mixes with the blood in the LAA 5. Due to the occluder portion 306 having the substantially non-permeable material associated therewith, if the medical tool 300 is properly positioned in the LAA 5, the fluid 304 may be substantially maintained within the LAA 5, but for general seeping around the outer periphery 314 of the medical tool 300 without an identifiable source or gap. The meaning of substantially maintaining fluid 304 in the LAA means substantially containing, sustaining and/or retaining the fluid in the LAA, except for general seeping along the outer periphery 314.

Figure 20A:
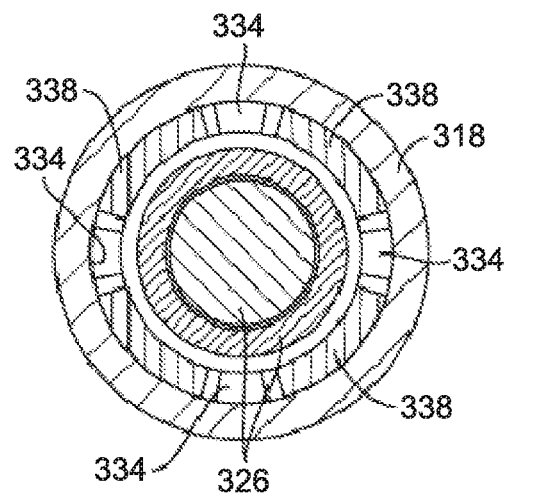
FIG. 20A is an enlarged cross-sectional view taken from region 20A of FIG. 20, depicting the flow path for the fluid at a distal portion of the delivery system, according to another embodiment of the present invention.
Figure 20B:
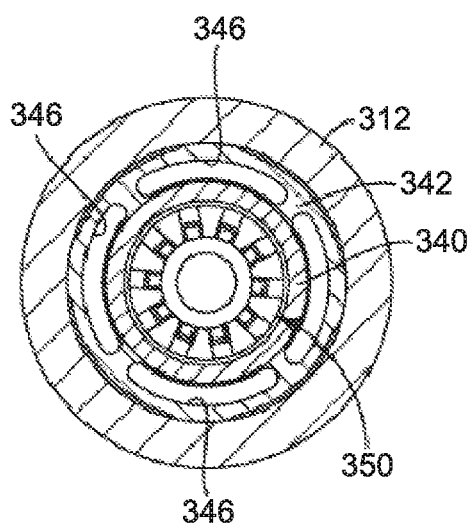
FIG. 20B is an enlarged cross-sectional view taken from region 20B of FIG. 20, depicting the flow path for the fluid at the hub of the medical tool, according to another embodiment of the present invention.

With respect to FIGS. 20, 20A, and 20B, the flow path (depicted by arrows 310 in FIG. 20) of the fluid 304 flowing from the delivery catheter 318 and through the hub 312 will now be described. The flow path 310 extends through the lumen 322 of the delivery catheter 318 and surrounds and moves along a length of the actuator shaft 326 and the delivery catheter 318. Section 20C identified in FIG. 20 may be substantially similar to that described and depicted in FIG. 18A, depicting the delivery catheter 318 defining the lumen 322 with the actuator shaft 326 positioned therethrough. The flow path 310 continues to advance along the collet 336 and then outward into a space 334 or channel defined between the collet fingers 338 (see FIGS. 20 and 20A). The flow path 310 continues advancing between an inner distal connector 340 and the delivery catheter 318 and then between the inner distal connector 340 and the medical tool 300 (only the hub 312 is shown), as depicted in FIGS. 20 and 20A. The hub 312 includes a guide ring 342 that may be embedded within the inner diameter or bore 344 defined in the hub 312 itself. Such guide ring 342 includes apertures 346 (see FIG. 20B) defined therein through which the flow path 310 extends. Such apertures 346 may include an annular space or partial annular configuration or space. In another embodiment, the inner diameter or bore may include an annular protrusion, instead of the guide ring 342, such that the bore 344 between the annular protrusion and the inner distal connector 340 may define an annular space through which the flow path 310 extends (instead of the apertures 346). Once the flow path 310 continues through the apertures 346 or annular space and past the guide ring 342 or annular protrusion in the bore 344, the flow path 310 continues advancing through the bore 344 of the hub 312 and distally over the inner distal connector 340. The inner distal connector 340 may include threads along an inner diameter thereof to couple to threads on a proximal end of the anchor hub 350. The flow path 310 continues advancing through the hub 312 until exiting the hub 312, as depicted with arrows 332, so that fluid 304 can enter the LAA 5 on the distal side of the medical tool 300, as shown in FIG. 19. With this arrangement, each of the handle 320, delivery catheter 318 and hub 312 of the medical tool 300 includes a common, shared, or corresponding flow path 310 that facilitates a fluid 304 to exit a distal side of the medical tool 300.

Figure 21:
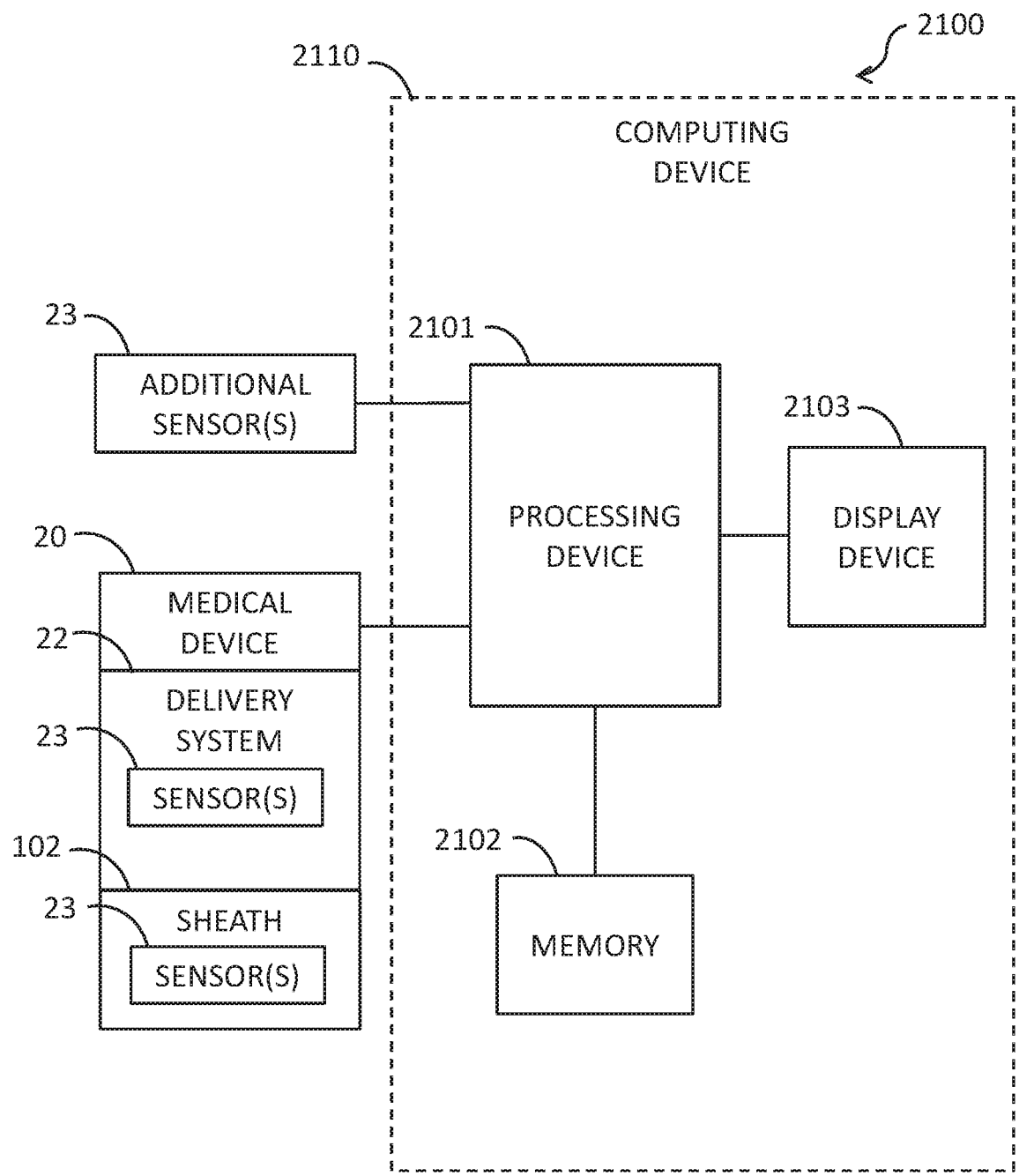
FIG. 21 is a block diagram illustrating example components of a medical system for occlusion detection.

With reference to FIG. 21 a system 2100 for occlusion detection may comprise sheath 102, delivery system 22, medical tool 20 and at least one sensor 23, as described above, and a processing device 2101. The system 2100 may further comprise a memory 2102 and a display device 2103. The processing device 2101, memory 2102 and display device 2103 may be part of a computing device 2110. The system 2100 may optionally comprise additional sensors located throughout the system. Computing device 2110 may also include an I/O interface, e.g., keyboard, mouse, printer, display device, touch screen, etc. The at least one sensor 23 may be a pressure sensor configured to detect the pressure within a target cavity. As noted above, in an embodiment, the at least one sensor 23 may be located on the distal portion of the sheath 102. Additionally or alternatively, the at least one sensor 23 may be located on the distal end of the delivery catheter 104. Additionally or alternatively, the at least one sensor 23 may be located on a proximal end of the delivery catheter 104. Additional sensors may be located elsewhere throughout the system. In an embodiment the at least one sensor 23 is configured to measure changes in pressure in known ways while blood is suctioned from the target cavity, or while fluid is injected into the target cavity, e.g., the LAA. By detecting changes in pressure within the cavity during suctioning of blood from the cavity, or during injecting of fluid into the cavity one can determine whether occlusion has been achieved. That is, if pressure or fluid resistance increases from a baseline pressure during fluid injection into the cavity, it can be inferred that occlusion has been achieved. Likewise, if pressure is detected as decreasing from a baseline during suctioning of blood from the cavity, then also it can be inferred that occlusion has been achieved. However, if pressure within the cavity remains unchanged from a baseline during suction of blood from the cavity, or during injection of fluid into the cavity, then it can be inferred that occlusion has not been achieved. In addition to comparing a curve representing detected pressure to a curve representing baseline pressure, inferences regarding whether occlusion has been achieved can be made by comparing a curve representing detected pressure with one or more pressure curves that would be expected when fluid is injected into the LAA or blood is suctioned from the LAA, when the LAA is in the fully open, fully occluded, and partially occluded conditions.

Because the delivery catheter 104 and/or sheath 102 are both open tubes from end-to-end, pressure within the cavity can be measured using an external pressure sensor 23 in known ways. Additionally or alternatively, in an embodiment, the at least one sensor 23 comprises at least one external pressure sensor that is connected to a proximal end of a lumen 108 of the delivery catheter 104. The distal end of the lumen 108 may be open to the blood pool of the target cavity, enabling the pressure of the target cavity to be measured directly. It is a known technique in medicine to measure an intra-cavity pressure within the human body using an external pressure measuring device, which eliminates the need for adding one or more pressure sensors to the tip of the delivery catheter or elsewhere within the cavity.

Processing device 2101 may include one or more processors. At least one processor of the processing device 2101 may be configured to process the pressure detected by the at least one sensor 23. In an embodiment, the processor 2101 is further configured to record the pressure detected by the pressure sensor over time.

Display device 2103 may include one or more displays configured to display the pressure detected by the at least one sensor 23. The display device 2103 may display the pressure detected by the at least one sensor 23 over time in a meaningful way such as a chart or a graph. In an embodiment, the display device 2103 may be further configured to display a baseline pressure next to, or on top of, the pressure detected by the at least one sensor 23 over time. In an embodiment, the processing device 2101 may be further configured to determine whether an occlusion is present by comparing the pressure detected by the at least one sensor 23 over time to a baseline pressure. The baseline pressure may be measured prior to the procedure to establish a baseline such that any change over time over a predetermined threshold subsequent to the deployment of the occluder portion can be used to infer that occlusion is ongoing or being achieved. In an embodiment, the processing device 2101 may be further configured to record measurements of pressure detected by the at least one sensor 23 over time. In an embodiment, the processing device 2101 may be configured to determine whether an occlusion is present by how fast the pressure changes over a period of time. The at least one sensor 23 may be in wired or wireless communication with processing device 2101. Display device 2103 may also be in wired or wireless communication with processing device 2101.

The system may further comprise a memory 2102. Memory 2102 may comprise storage for storing data. In an embodiment, memory 2102 is configured to store the measurements of pressure detected by the at least one sensor 23. In a further embodiment, memory 2102 is configured to store the baseline pressure. The memory 2102 may include any volatile and/or non-volatile memory, such as random-access memory or a hard disk drive.

Figure 22:
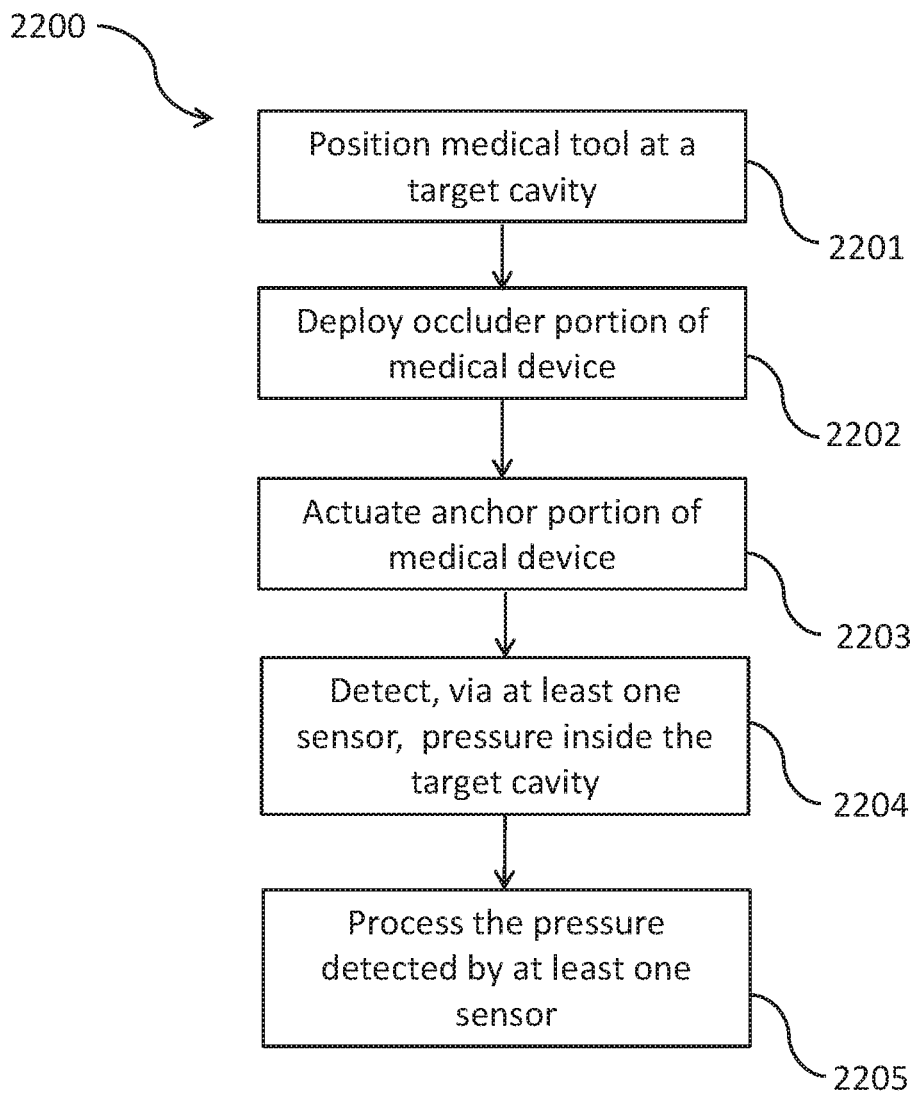
FIG. 22 is a flowchart illustrating a method of occlusion detection.

With reference to FIG. 22, at step 2201 the medical tool 20 may be positioned within an organ of a patient at a target location, such as the LAA, as described above. At step 2202, the occluder portion 24 of the medical tool 20 may be deployed, as described above. At step 2203, upon the occluder portion 24 being in an expanded, deployed position, the anchor portion 26 of the medical tool 20 may go from a retracted position to an anchor deployed position having tines, as described above. At step 2204, the pressure inside the target cavity is detected via at least one sensor 23.

In an embodiment, the detecting step 2204 is performed while blood is being suctioned from inside the target cavity, creating a vacuum. Additionally or alternatively, a pressure measurement may be performed directly using an external pressure sensor that is connected to a proximal end of a lumen of the delivery catheter. The distal end of the lumen may be open to the blood pool of the target cavity, enabling the pressure of the target cavity to be measured directly. At step 2205, the processing device 2101 processes the pressured detected by the at least one sensor 23. The presence or absence of an occlusion is determined by the pressure within the target cavity. In an embodiment, the method further comprises recording, via the processing device 2101, the pressure over time. In a further embodiment, the method further comprises storing, in a memory, pressure measurements detected by the at least one sensor 23 over time. The presence or absence of an occlusion may be determined by comparing the baseline pressure measurement to the pressure detected by the sensor over time. In an embodiment, the method further comprises determining, via the processing device 2101, the presence or absence of an occlusion by comparing the baseline measurement to the pressure detected by the at least one sensor 23 over time.

Figure 23:
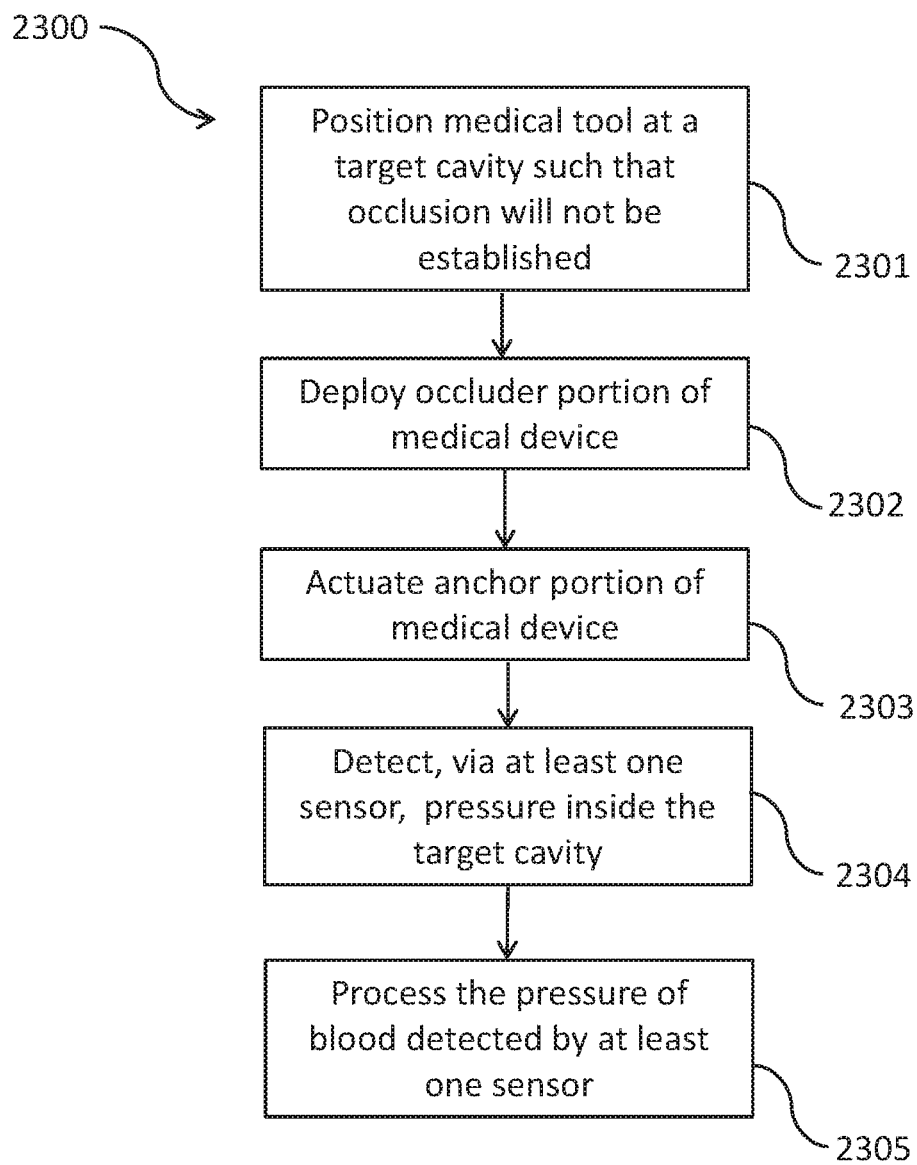
FIG. 23 is a flowchart illustrating a method of determining a baseline measurement of a patient for occlusion detection.

With reference to FIG. 23, in an embodiment, a baseline pressure measurement of a patient at the relevant anatomic location, e.g., the LAA, may be determined and then used as a reference to determine if there is a full or partial occlusion. At step 2301 the medical tool 20 may be positioned within an organ of a patient at a target location, such as the LAA of the heart, as described above. However, the medical tool 20 is positioned such that there will not be full occlusion. At step 2302, the occluder portion of the medical tool 20 may be deployed, as described above. At step 2303, upon the occluder portion being in an expanded, deployed position, the anchor portion of the medical tool may go from a retracted position to an anchor deployed position having tines, as described above. At step 2304, pressure inside the target cavity is detected via at least one sensor 23. At step 2305, the processing device 2101 processes the pressure detected by the at least one sensor 23 and determines a baseline pressure of blood inside the cavity. The methods described and illustrated in relation to FIGS. 22 and 23 are also algorithms that can be utilized by a skilled software engineer to generate the requisite step-by-step computer codes for implementation of the overall method in a computer system (e.g., a general-purpose computer or a special purpose computer such as the Carto® system (available from Biosense Webster, Inc. of Irvine, Calif.) so that embodiments described herein can be used to detect occlusion.

In an embodiment, the method may further comprise determining, via the processing device 2102, the presence or absence of an occlusion by comparing the baseline pressure measurement to the detected pressure over time. Additionally or alternatively, the method may further comprise determining, via the processing device 2102, the presence or absence of an occlusion by how fast the pressure changes over a period of time.

In an embodiment, the method may further comprise recording, via the processing device 2101, the measurements of the pressure over time. In a further embodiment, the method may further comprise storing, in the memory 2102, measurements of the pressure over time.

It should be understood that many variations are possible based on the disclosure herein. Although features and elements are described above in particular combinations, each feature or element can be used alone without the other features and elements or in various combinations with or without other features and elements.

What is claimed is:

1. A system for occlusion detection comprising:
   a sheath having a length and a sheath lumen extending through the length of the sheath;
   a delivery system comprising:
      a delivery catheter extending between a proximal end and a distal end; and
      a handle coupled to the proximal end of the delivery catheter;
   a medical tool coupled to a distal end of the delivery catheter configured to be inserted at a target cavity within a portion of an organ of a patient, the target cavity being a left atrial appendage, the medical tool comprising:
      a hub including a bore defining an axis;
      an occluder portion coupled to the hub, the occluder portion configured to be moved to an occluder non-deployed position with the occluder portion within a distal portion of the sheath, and the occluder portion configured to be moved to an occluder deployed position upon the sheath being moved proximally relative to the occluder portion; and
      an anchor portion extending between a first end and a second end, the anchor portion having tines configured to engage tissue, the first end being coupled to the handle, the second end being pivotably coupled to a distal end portion of the occluder portion, wherein, upon the occluder portion maintaining the occluder deployed position, the anchor portion is pivotable relative to the occluder portion between an anchor non-deployed position and an anchor deployed position;
   at least one pressure sensor configured to directly measure a pressure of a blood pool in the left atrial appendage while blood is being suctioned from inside the left atrial appendage; and
   at least one processor configured to process the pressure measurement acquired from the at least one pressure sensor, the processor also configured to compare the pressure acquired from the at least one pressure sensor to a baseline pressure measurement of a left atrial appendage to determine the presence or absence of an occlusion;
   wherein the medical tool is arranged for positioning at the left atrial appendage with the occluder portion maintained in the occluder deployed position and the anchor portion pivoted to the anchor deployed position such that occlusion is not established, and wherein the delivery catheter injects a fluid through the hub and into the left atrial appendage as the baseline pressure measurement.

2. The system of claim 1, wherein the at least one pressure sensor is located on a distal portion of the sheath.

3. The system of claim 1, wherein the at least one pressure sensor is located on the distal end of the delivery catheter.

4. The system of claim 1, wherein the at least one pressure sensor is located on a proximal end of the delivery catheter.

5. The system of claim 1, wherein the processor is further configured to record measurements of pressure detected by the at least one pressure sensor over time.

6. The system of claim 5, further comprising a memory configured to store the measurements of the pressure detected by the at least one pressure sensor over time.

7. The system of claim 5, further comprising a display configured to display the pressure detected by the at least one pressure sensor over time.

8. The system of claim 7, wherein the display is further configured to display a baseline characteristic of blood side by side or on top of the pressure detected by the at least one pressure sensor over time.

9. The system of claim 5, wherein the processor is further configured to determine whether an occlusion is present by how fast the pressure changes over a period of time.

* * * * *

UNITED STATES PATENT AND TRADEMARK OFFICE
CERTIFICATE OF CORRECTION

PATENT NO. : 11,589,873 B2
APPLICATION NO. : 16/720978
DATED : February 28, 2023
INVENTOR(S) : Eid Adawi et al.

It is certified that error appears in the above-identified patent and that said Letters Patent is hereby corrected as shown below:

On the Title Page
In Item (57), under "ABSTRACT", in Column 2, Line 13, delete "form" and insert -- from --, therefor.

In the Specification
In Column 4, Line 52, delete "invention." and insert -- invention; --, therefor.
In Column 5, Line 53, delete "pressured" and insert -- pressure --, therefor.
In Column 12, Line 1, delete "Touhy" and insert -- Tuohy --, therefor.
In Column 14, Line 33, delete "or a" and insert -- or in a --, therefor.
In Column 15, Line 59, delete "impassible" and insert -- impassable --, therefor.
In Column 16, Line 43, delete "a may" and insert -- may --, therefor.
In Column 16, Line 43, delete "proximal a" and insert -- proximal to a --, therefor.
In Column 18, Line 38, delete "Heprin." and insert -- Heparin. --, therefor.
In Column 22, Lines 9-10, delete "pressured" and insert -- pressure --, therefor.

Signed and Sealed this
Fifth Day of September, 2023

Katherine Kelly Vidal
*Director of the United States Patent and Trademark Office*